United States Patent
Nielsen et al.

(10) Patent No.: US 12,161,455 B2
(45) Date of Patent: Dec. 10, 2024

(54) MOTION COMPENSATED MAGNETIC RESONANCE IMAGING

(71) Applicant: KONINKLIJKE PHILIPS N.V., Eindhoven (NL)

(72) Inventors: Tim Nielsen, Hamburg (DE); Jan Hendrik Wuelbern, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1037 days.

(21) Appl. No.: 16/954,258

(22) PCT Filed: Dec. 18, 2018

(86) PCT No.: PCT/EP2018/085513
§ 371 (c)(1),
(2) Date: Jun. 16, 2020

(87) PCT Pub. No.: WO2019/121693
PCT Pub. Date: Jun. 27, 2019

(65) Prior Publication Data
US 2020/0405176 A1    Dec. 31, 2020

(30) Foreign Application Priority Data
Dec. 18, 2017  (EP) .................................... 17208013

(51) Int. Cl.
*A61B 5/055* (2006.01)
*G01R 33/48* (2006.01)
(Continued)

(52) U.S. Cl.
CPC ............ *A61B 5/055* (2013.01); *G01R 33/482* (2013.01); *G01R 33/4826* (2013.01);
(Continued)

(58) Field of Classification Search
CPC .. A61B 5/055; G01R 33/482; G01R 33/4826; G01R 33/5601; G01R 33/5612; G01R 33/56509; G01R 33/5676
See application file for complete search history.

(56) References Cited

U.S. PATENT DOCUMENTS

2005/0113961 A1* 5/2005 Sabol ..................... A61B 5/055
700/182
2013/0310655 A1* 11/2013 Sachs ..................... A61B 6/037
600/301
(Continued)

OTHER PUBLICATIONS

Lee, G., et al., "Quantitative self-gated free breathing 4D DCE MRI of the liver with retrospectively selectable temporal resolution," Proc. Intl. Soc. Mag. Resonance. vol. 21, 2013. p. 4083 (Year: 2013).*

(Continued)

*Primary Examiner* — Sean A Frith

(57) ABSTRACT

The invention provides for a medical imaging system (100, 300, 500) comprising a processor (104). Machine executable instructions cause the processor to: receive (200) magnetic resonance data (120) comprising discrete data portions (612) that are rotated in k-space; bin (202) the discrete data portions into predetermined motion bins (122) using a motion signal value; reconstruct (204) a reference image (124) for each of the predetermined motion bins; construct (206) a motion transform (126) between the reference images; bin (208) a chosen group (610) of the discrete data portions into a chosen time bin (128). Generate an enhanced image (130) for the chosen time bin using the chosen group fo the discrete data portions and the motion transform of each of the chosen group to correct the discrete data portions.

18 Claims, 10 Drawing Sheets

(51) Int. Cl.
  *G01R 33/56* (2006.01)
  *G01R 33/561* (2006.01)
  *G01R 33/565* (2006.01)
  *G01R 33/567* (2006.01)
(52) U.S. Cl.
  CPC ..... *G01R 33/5601* (2013.01); *G01R 33/5612* (2013.01); *G01R 33/56509* (2013.01); *G01R 33/5676* (2013.01)

(56) References Cited

U.S. PATENT DOCUMENTS

| | | | |
|---|---|---|---|
| 2014/0035582 A1* | 2/2014 | Boernert | G01R 33/565 324/312 |
| 2015/0077112 A1 | 3/2015 | Otazo et al. | |
| 2015/0091563 A1* | 4/2015 | Lu | A61B 5/055 324/309 |
| 2015/0226815 A1 | 8/2015 | Block et al. | |
| 2015/0276909 A1 | 10/2015 | Kawaji et al. | |
| 2015/0327783 A1 | 11/2015 | Wang et al. | |
| 2016/0082288 A1* | 3/2016 | Vahala | A61B 5/742 600/411 |
| 2016/0104279 A1* | 4/2016 | Li | A61B 5/0044 382/131 |
| 2016/0109539 A1* | 4/2016 | Mardor | A61B 5/055 600/420 |
| 2016/0274201 A1 | 9/2016 | Zhu et al. | |

OTHER PUBLICATIONS

Adam Johansson et al., "Rigid-Body Motion Correction of the Liver in Image Reconstruction for Golden-Angle Stack-of-Stars" Magnetic Reson in Med. (2017).

Thomas Benkert et al., "Free-Breathing Volumetric Fat/Water Separation by Combining Radial Sampling, Compressed Sensing, and Parallel Imaging" Magnetic Reson. in Med. 78 p. 565-576 (2017).

Feng et al., "XD-GRASP: Golden-Angle Radial MRI with Reconstruction of Extra Motion-State Dimensions Using Compressed Sensing" Magnetic Reson. in Med 75 p. 775-788 (2016).

Piccini et al., "Four-Dimensional Respiratory Motion-Resolved Whole Heart Coronary MR Angiography" Magnetic Reson. in Med. 77 p. 1473-1484 (2017).

Rank et al., "4D Respiratory Motion-Compensated Image Reconstruction of Free-Breathing Radial MR Data With Very High Undersampling" Magnetic Reson. in Med. 77 p. 1170-1183 (2017).

Zhou et al., "Accelerated Noncontrast-Enhanced 4-Dimensional Intracranial MR Angiography Using Golden-Angle Stack-of-Stars Trajectory and Compressed Sensing With Magnitude Subtraction" Magn Reson Med 79 p. 867-878 (2018).

Yang et al., "Free-Breathing, Motion-Corrected, Highly Efficient WholeHeart T2 Mapping at 3T with Hybrid Radial-Cartesian Trajectory" Magnetic Reson. in Med. 75 p. 126-136 (2016).

Han et al "Segmented Golden Ratio Radial Reordering with Variable Temporal Resolution for Dynamic Cardiac MRI" Magnetic Reson. in Med. 76 p. 94-103 (2016).

International Search Report and Written Opinion from PCT/EP2018/085513 mailed Apr. 5, 2019.

Fujimoto et al "GRASP with Motion Compensation for DCE-MRI of the Abdomen" Proceedings of the International Society for Magnetic Reson. in Med. Apr. 22-27, 2017 p. 2009.

Feng et al "RACER-GRASP Respiratory Weighted Aortic Contrast Enhancement Guided and Coil Unstreaking Golden Angle Radial Sparce MRI" Magnetic Reson. in Med. 80 p. 77-89 (2017).

Chen et al "MR ARTS-GROWL" A Non-Iterative Motion Resistant Technique for High Spatiotemporal Live DCE Imaging Proceedings of the International Soc. for Magnetic Reson. in Med. Aptil 22-27 p. 3208 (2017).

Wulbern et al "Improved Reconstruction of Free Breathing Abdominal Imaging Using non-Cartesian Iterative Reconstruction and Elastic Image Registration" Proceedings of the International Soc. for Mag. Reson. in Med. p. 4005 Apr. 7, 2017.

* cited by examiner

MOTION COMPENSATED MAGNETIC RESONANCE IMAGING

CROSS REFERENCE TO RELATED APPLICATIONS

This application is a U.S. national phase application of International Application No. PCT/EP2018/085513 filed on Dec. 18, 2018, which claims the benefit of EP Application Serial No. 17208013.7 filed on Dec. 18, 2017 and is incorporated herein by reference.

FIELD OF THE INVENTION

The invention relates to magnetic resonance imaging, in particular to dynamic contrast enhanced magnetic resonance imaging.

BACKGROUND OF THE INVENTION

A large static magnetic field is used by Magnetic Resonance Imaging (MRI) scanners to align the nuclear spins of atoms as part of the procedure for producing images within the body of a patient. This large static magnetic field is referred to as the B0 field or the main magnetic field. Various quantities or properties of the subject can be measured spatially using MRI. Several quantities which may be measured quantitatively measured are the relaxation times related to the decay of a Nuclear Magnetic Resonance (NMR) signal. For example the T1 relaxation time can be measured using T1 weighted pulse sequences. Magnetic resonance imaging contrast agents can be injected into a subject which may cause a large change in the local T1 relaxation time. If a contrast agent is injected into an artery magnetic resonance imaging system can be used to track the spread of the contrast agent through the subject. T1 weighted image will therefore provide a stark contrast between blood with contrast agent and tissues immediately adjacent to the blood.

United States patent application 2015/0327783 discloses a method for non-contrast enhanced 4D time resolved dynamic magnetic resonance angiography using arterial spin labeling of blood water as an endogenous tracer and a multiphase balanced steady state free precession readout is presented. Imaging can be accelerated with dynamic golden angle radial acquisitions and k-space weighted imaging contrast (KWIC) image reconstruction and it can be used with parallel imaging techniques. Quantitative tracer kinetic models can be formed allowing cerebral blood volume, cerebral blood flow and mean transit time to be estimated. Vascular compliance can also be assessed using 4D dMRA by synchronizing dMRA acquisitions with the systolic and diastolic phases of the cardiac cycle.

SUMMARY OF THE INVENTION

The invention provides for a medical imaging system, a computer program product and a method in the independent claims. Embodiments are given in the dependent claims.

A difficulty in performing dynamic contrast enhanced magnetic resonance imaging is that there are different processes happening on different time scales. For example after a contrast agent has been administered, the contrast agent will move to the area of interest or organ of interest with the flow of blood. There may be a narrow time window when the contrast agent first enters the area of interest and then may decrease. The time period when we are interested to image the subject is referred to as the chosen time bin herein. The subject may also experience motion, such as breathing. If the subject moves during the chosen time bin, it will corrupt the data.

To make a magnetic resonance image in this situation, the magnetic resonance data is continuously acquired as discrete data portions. The discrete data portions are acquired using a k-space trajectory that rotates from acquisition to acquisition. At the same time as a discrete data portion is acquired, a motion signal value is recorded which is descriptive of the motion of the subject.

Once the data has been acquired, the discrete data portions are all sorted or binned into predetermined motion bins. All of the magnetic resonance data one of these bins represents the same motion state. Then a reference image is reconstructed from the discrete data portions for each of the predetermined motion bins. Since the bins contain discrete data portions from many times the k-space is well sampled and the reference images may be of high quality.

There is then a second binning of the discrete data portions where discrete data portions which occurred during the time period of the chosen time bin are selected. The discrete data portions within the chosen time bin contain information about the changes in the contrast due. However, the individual discrete data portions may have been acquired for different motion states of the subject. As is described in detail below, contrast data from each of the individual discrete data portions is extracted and superimposed on the reference image for one of the predetermined motion bins using an iterative process.

In one aspect, the invention provides for a medical imaging system. A medical imaging system as used herein may encompass a system for image processing and/or for acquiring medical image data and performing image processing tasks. The medical imaging system comprises a memory for storing machine-executable instructions. The medical imaging system further comprises a processor. Execution of the machine-executable instructions causes the processor to receive magnetic resonance data. The magnetic resonance data comprises discrete data portions. Each data portion comprises an acquisition time and comprises a motion signal value. The motion signal value may for example be data that are appended to the discrete data portion or it may also include data which is located within the k-space samples of the discrete data portions.

For example, it may be data which is contained in a navigator or self-navigation in the acquired magnetic resonance data. The discrete data portions have a sampling pattern in k-space.

Execution of the machine-executable instructions further cause the processor to bin the discrete data portions into predetermined motion bins using the motion signal value for each of the discrete data portions. The motion signal value may for example be descriptive of a motion phase or position of a subject when the magnetic resonance data was acquired. By binning the discrete data portions into the predetermined motion bins the magnetic resonance data are sorted according to the position or motion state that the subject had when the particular discrete data portion was acquired.

Execution of the machine executable instructions further cause the processor to reconstruct a reference image for each of the predetermined motion bins using the binned discrete data portions. In this step all of the data within a particular motion bin is used to reconstruct an image. Execution of the machine-executable instructions further cause the processor to construct a displacement vector field between a selected motion bin and each of the predetermined motion bins using the reference image for each of the predetermined motion bins. One of the reference images which was reconstructed for each of the predetermined motion bins is then selected and a displacement vector field is created so that there is a mapping between this chosen image and the predetermined reference image for each of the other predetermined motion bins.

References to displacement vector field herein may be replaced with the term motion transform.

The selected motion bin is selected from one of the predetermined motion bins. The selected motion bin may in some cases be arbitrary or it may be chosen so that a particular position of the subject is illustrated. Execution of the machine-executable instructions further causes the processor to bin a chosen group of the discrete data portions into a chosen time bin using the acquisition time of each of the discrete data portions. In this step the discrete data portions of the magnetic resonance data are binned a second time. In this time, instead of using the motion signal value, the acquisition time is used for the binning. This may be useful when the time something happens is of importance for the resulting medical images. For example, after a contrast agent has been injected into a subject it may be useful to make images at a particular time range to note the optimal effect of this contrast agent.

Execution of the machine-executable instructions further cause the processor to generate an enhanced image for the chosen time bin using the chosen group of the of the discrete data portion into a chosen time bin using the chosen group of the discrete data portions and the motion transform of each of the chosen group to correct the discrete data portions. This for example may be achieved either in image or k-space.

In another embodiment, execution of the machine-executable instructions further causes the processor to iteratively generate an enhanced image for the chosen time bin. The enhanced image is initially the reference image of the selected motion bin. The iterative generation of the enhanced image is performed by repeating the following for each of the discrete data portions of the chosen group. In this iterative process first a current data portion is chosen from the discrete data portions that are a member of the chosen group. The current data portion is binned into a current motion bin. The current motion bin is one of the predetermined motion bins. The iterative process further comprises calculating a transformed image by transforming an enhanced image using the displacement vector field between the selected motion bin and the current motion bin.

The iterative process further comprises transforming the transformed image into transformed k-space data. The iterative process further comprises calculating a k-space difference between the k-space data of the current data portion and corresponding k-space data points of the transformed k-space data. In this step the individual samples in k-space of the current data portion are compared to the k-space data of the transformed k-space data. The iterative process further comprises transforming the k-space difference into a difference image. The iterative process further comprises transforming the difference image into a modified difference image by using an inverse of the displacement vector field between the selected motion bin and the current motion bin and then the iterative process further comprises updating the enhanced image by adding the modified difference image to the enhanced image. This is then repeated so that it is performed for each of the discrete data portions that are members of the chosen group. This may have the advantage that the particular reference image of the selected motion bin is enhanced with contrast data from the discrete data portions of the chosen group. It may be able to compensate for the motion of a subject when the motion is changing relatively fast to changes in the contrast over the time period of the chosen time bin. This may function effectively because the rotation of the sampling pattern in k-space has an effect of sampling predominantly within a central k-space region. The central k-space region is largely responsible for the image contrast and it can be fully covered by using only relatively few discrete data portions.

The higher k-space data surrounding the central k-space region is predominantly responsible for the fine structure or details within an image. The fine detail image is taken from a large time period by binning the magnetic resonance data and its discrete data portions into the predetermined motion bins. Changes in contrast are then selected for the particular chosen time bin. The displacement vector fields are then used with the above descriptive of the iterative process to compensate for motion.

In should be noted that in the above described iterative process, the updating of the enhanced image can be performed in different ways. In some embodiments, after each current data portion has been processed the modified difference image can be added to the enhanced image immediately before the next loop of the iteration. Another possibility is that the modified difference image for each of the discrete data portions for the chosen group are stored and then added to the enhanced image at once.

In some embodiments each of the discrete data portions for the chosen group is processed only once.

In some other embodiments the iterative process for each of the discrete data portions for the chosen group is cycled through multiple times. After each cycle of the discrete data portions for the chosen group, the convergence of the enhanced image can be checked. If the enhanced image has converged within a predetermined convergence criteria then the iterative loop can be ended.

In another embodiment, the sampling pattern is rotated in k-space between sequentially acquired discrete data portions. The discrete data portions may represent a trajectory or path in k-space which is acquired during a magnetic resonance imaging protocol. For example, the sampling pattern in k-space could be a linear blade which is then rotated in space or the sampling pattern in k-space could also be something such as a spiral or curved trajectory which is sampled in k-space.

In another embodiment, execution of the machine-executable instructions further causes the processor to store, display or provide the enhanced image after the iterative process is finished.

In another embodiment, the medical imaging system further comprises a magnetic resonance imaging system. The medical imaging system further comprises a subject motion detection system configured for measuring the motion signal value. The memory further contains pulse sequence commands. The pulse sequence commands are configured for acquiring the magnetic resonance data according to a continuous sampling magnetic resonance protocol. One example of a continuous sampling magnetic resonance protocol is a free breathing magnetic resonance protocol, where the discrete data portions of the magnetic resonance data are continuously acquired. Because the data is continuously acquired the subject being imaged does not need to make a breath hold during data acquisition. Another example would be a continuous sampling magnetic resonance angiography protocol.

A continuous sampling pulse sequence may contain elements which only do magnetization/contrast preparation (e.g. fat suppression/inversion pulses). These elements may interrupt the timing of the data acquisition so "continuous sampling" does not imply that the sampling is perfectly continuous.

For example, after one fat suppression pulse, 50 spokes (or 50 discrete data portions) may be acquired. After this there is the next fat suppression pulse followed by another 50 spokes. In this example, the timing of the data portions which are acquired within one block of the 50 spokes is closer than between spokes which are interrupted by a fat suppression pulse. In this example, the differences in timing are on the order of 100 ms so much shorter than any motion cycle of interest. So "continuous" could be understood as not being triggered or gated by patient physiology. An alternative naming of "continuous sampling magnetic resonance protocol" could be "continuous block sampling magnetic resonance protocol.

Execution of the machine-executable instructions further cause the processor to control the magnetic resonance imaging system with the pulse sequence commands to acquire the magnetic resonance data. Execution of the machine-executable instructions further cause the processor to control the magnetic resonance imaging system to acquire the motion signal during or sequential to acquisition of the magnetic resonance data.

The subject motion detection system may take different forms in different embodiments or examples. For example the subject motion detection system may be an external system that measures the position of the subject. In other examples the subject motion detection system may be a software module or addition to the magnetic resonance imaging system. The tracking of fiducial markings and/or the acquisition of navigator data or even using portions of the k-space data that are repeatedly sampled in the discrete data portions themselves may be used or considered to be part of the subject motion detection system.

In another embodiment, execution of the machine-executable instructions further causes the processor to append the motion signal to the magnetic resonance data. In the instance where there is a separate subject motion detection system this may include appending the data or storing it with the magnetic resonance data. In the case where a navigator or self-navigation is used this may represent processing of the magnetic resonance data.

In another embodiment, the subject motion detection system comprises the magnetic resonance imaging system. The pulse sequence commands are adapted for acquiring the magnetic resonance navigator data during or sequential to the acquisition of the magnetic resonance data. Execution of the machine-executable instructions further cause the processor to calculate the motion signal at least partially using the magnetic resonance navigator data. This may be advantageous because the motion signal can be derived without additional hardware modifications to the magnetic resonance imaging system. The magnetic resonance navigator data could for example be acquired by having alternating pulse sequences where one of the pulse sequences acquires the magnetic resonance navigator data. This may for example be in an interleaved fashion or it could be data that is acquired when the discrete data portions are acquired. In some instances, the discrete data portions are sufficiently sampled that the discrete data portions themselves contain the magnetic resonance navigator data.

In another embodiment, the continuous sampling magnetic resonance protocol is a dynamic contrast enhanced magnetic resonance imaging protocol.

In another embodiment, the subject motion detection system comprises any one of the following: a cardiac motion detector, an ECG, a VCG, a pulseoximeter, a respiratory belt, a breath sensor, an optical motion detector, a camera system, a 3D camera system, an optical fiducial marker detector system, a magnetic resonance fiducial marker detector system and combinations thereof. Any or combinations of the previously mentioned possibilities may be combined to generate a motion signal which may be descriptive of the motion of a subject.

In another embodiment, the magnetic resonance data is parallel imaging magnetic resonance data. The difference image incorporates k-space differences from multiple magnetic resonance coil elements. For example using the coil sensitivity matrix the transformed-k-space data may be calculated for each antenna element. The k-space difference may therefore be calculated for each antenna element of the magnetic resonance imaging system. This may provide for more accurate calculating of the enhanced image.

In another embodiment, the memory contains coil sensitivity data. Execution of the machine-executable instructions further causes the processor to correct the reference image for each of the predetermined motion bins by correcting the coil sensitivity data using the vector displacement fields. This may be beneficial because the coil sensitivity data may for example be measured for only one motion phase of the subject. This may provide for a means of using a single set of coil sensitivity data for one known motion state of the subject. This can then be transformed into the different motion states.

In another embodiment, execution of the machine-executable instructions further causes the processor to acquire coil sensitivity data for each of the predetermined motion bins. The reference image for each of the predetermined motion bins is calculated using this coil sensitivity data. This may be beneficial because in parallel imaging systems this may provide for improved calculation of the enhanced image.

As an alternative, low resolution images of individual receive channels which are reconstructed for each motion state (using the binned data) can be used to create coil sensitivity maps for all motion states from a single set of CSMs that are available for one motion state.

In another embodiment, execution of the machine-executable instructions further causes the processor to bin the discrete data portions into predetermined time bins. Execution of the machine-executable instructions further cause the processor to iteratively generate the enhanced image for each of the predetermined time bins by setting the chosen time bin to each of the predetermined temporal bins. This may be beneficial because it may provide for a means of making an animation or a series of enhanced images which represent each of the predetermined time bins. This for example may be useful in studying or displaying the progress of a contrast agent over a variety of times.

In another embodiment, the reference image for initializing the enhanced image for each of the predetermined time bins is identical. This may be beneficial because then each of the enhanced images is then shown for the same motion state of the subject.

In another embodiment, execution of the machine-executable instructions further causes the processor to transform the reference image for each of the predetermined time bins to a common motion state using the displacement vector fields. This embodiment may also be beneficial because it provides for the set of enhanced images to be in a common motion state.

In another embodiment execution of the machine-executable instructions further cause the processor to process the modified difference image with a regularization algorithm before adding the modified difference image to the enhanced image. A regularization algorithm as used herein encompasses an algorithm which is used for transforming an image to reduce noise or improve image quality. The use of a regularization algorithm may improve the overall quality of the enhanced image. This may also help remove noise from the modified difference image.

In some cases, that data simulated from the reconstructed image exactly not match the acquired data. E.g. because the acquired data are contaminated by noise, or because the simulation model has systematic errors (e.g. inaccurate coil sensitivity maps, errors in the motion model). Thus, a reconstruction algorithm that only minimizes the data error usually could possibly a point where image quality degrades (although the data error still decreases) because the image is modified such that the simulated data match the measurements better than can be expected. Possible consequences are e.g. excessive noise in the image or systematic artifacts.

This can be counteracted by introducing one or more additional terms in the minimization function which somehow quantify image quality. This procedure is termed regularizing the minimization problem. The choice of the specific regularization terms which are used is based on heuristics. Consequently, there is a large variety of regularization terms which are commonly used. E.g. the L2-norm of the image (Tichonov regularization), the L1-norm of image gradients (total variation), nuclear norm, sparse representation in the wavelet domain or some other basis like application specific dictionaries.

Typically, regularization for an iterative minimization algorithm is implemented by one of the following two options:
1. The image update which is computed based on the data difference is modified according to the regularization term before it is added to the current image.
2. Within the iteration loop the image is modified twice: First the update calculated from the data difference is added to the image and then the image is modified according to the regularization term.

In another embodiment, the enhanced image for each of the predetermined time bins is descriptive of a single motion state as defined by the motion signal value.

In another embodiment, execution of the machine-executable instructions further causes the processor to calculate an elastic registration for the reference image of each of the predetermined motion bins. The displacement vector field is interpolated for each of the current data portions using the elastic registration. This may be beneficial because it may account for small variations of the motion signal value within a particular predetermined motion bin. This may provide for improved calculation of the enhanced image.

In another embodiment, the chosen time bin has a central time. The k-space differences is weighted by a weighting factor dependent upon a time difference between the central time and the acquisition time of the current data portion. As the time difference decreases the weighting factor increases. This may be beneficial because it may provide for contrast information which is closer to the central time to have a larger effect on the enhanced image.

In another embodiment, the sampling pattern in k-space of the discrete data portion is a spiral trajectory.

In another embodiment, the sampling pattern in k-space of the discrete data portions is a linear trajectory.

In another embodiment the sampling pattern of the discrete data portions is rotated in k-space between sequentially acquired discreet data portions. This for example may be useful when the sampling pattern is a spiral or linear trajectory. The rotation of the sampling patterns provides for a central region which is oversampled and then another region which is more sparsely sampled.

In another embodiment the sampling pattern of the discrete data portions is a Cartesian sampling pattern.

In another embodiment the sampling pattern of the discrete data portions oversamples a central region of k-space. This for example may be useful in correcting for motion.

In another embodiment the sampling pattern of the discrete data portions is adapted to a motion pattern of the subject. This may be useful because the sampling pattern can be used for compensating for motion of the subject.

In another embodiment the sampling pattern of the discrete data portions is randomly or pseudo randomly selected. This may be beneficial because it may help provide for a more complete sampling of k-space before the enhanced image is reconstructed.

In another embodiment generating the enhanced image is performed by calculating transformed k-space data by transforming each of the discreet data portions of the chosen group using its motion transform. These for example may be rigid body transformations which are straight forward to calculate in the corresponding k-space. The generation of the enhanced image is further performed by generating combined k-space data by combining the k-space data of the selected motion bin with the transformed k-space data of each of the discreet data portions. This may be performed in several different ways. In one way the k-space data may be simply added to the existing k-space data. In other examples the k-space data present in the selected motion bin may be replaced by the transformed k-space data. The generation of the enhanced image is further performed by reconstructing the enhanced image from the corrected k-space data. This may for example be a simple transformation from k-space into image space.

In each of these cases the transformation of the k-space data using the motion transform is performed such that the ending state of the transformed k-space data is the same as the selected motion bin.

In another embodiment the k-space data of the selected motion bin within a predetermined distance of the k-space data of each of the discreet data portions is replaced with the transformed k-space data of each of the discreet data portions. In this example the k-space data of the selected motion bin which is within a certain distance of the transformed k-space data is replaced.

In another embodiment the transformed k-space data is calculated using phase shifts and rotations in k-space determined using the motion transform. These phase shifts and rotations correspond to rigid body transformations in image space.

In another embodiment the combined k-space data is formed by calculating a weighted sum of data using a gated window function of the selected motion bin. This may be useful because k-space data which is closer to the specified motion state are given more weight in modifying the resulting image.

In another aspect, the invention provides for a method of image processing. The method comprises receiving magnetic resonance data. The magnetic resonance data comprises discrete data portions. Each data portion comprises an acquisition time and comprises a motion signal value. The discrete data portions have a sampling pattern in k-space. The sampling pattern is rotated in k-space between sequentially acquired discrete data portions. The method further comprises binning the discrete data portions into the predetermined motion bins using the motion signal value of each of the discrete data portions. The method further comprises reconstructing a reference image for each of the predetermined motion bins using the bin discrete data portions.

The method further comprises constructing a displacement vector field between a selected motion bin and each of the predetermined motion bins using the reference image for each of the predetermined motion bins. The selected motion bin is selected from the predetermined motion bins. The method further comprises binning a chosen group of the discrete data portions into a chosen time bin using the acquisition time of each of the discrete data portions.

The method further comprises generating an enhanced image for the choen time bin using the chosen group of the discrete data portions and the motion transform of each of the chosen group to correct the discrete data portions In another embodiment, the method further comprises iteratively generating an enhanced image for the chosen time bin. The enhanced image is initially the reference image of the selected motion bin. The iterative generation of the enhanced image is performed by repeating the following for each of the discrete data portions of the chosen group. The iterative process comprises choosing a current data portion from the discrete data portions of the chosen group.

The current data portion was binned into a current motion bin. The current motion bin is one of the predetermined motion bins. The iterative process further comprises calculating a transformed image by transforming the enhanced image using the displacement vector field between the selected motion bin and the current motion bin. The iterative process further comprises transforming the transformed image into transformed k-space data. The iterative process further comprises calculating a k-space difference between k-space data of the current data portion and corresponding k-space data points of the transformed k-space data.

The iterative process further comprises transforming the k-space difference into a difference image. The iterative process further comprises transforming the difference image into a modified difference image by using an inverse of the displacement vector field between the selected motion bin and the current motion bin. The iterative process further comprises updating the enhanced image by adding the modified difference image to the enhanced image. The advantages of this method of image processing has been previously disclosed.

The method of image processing may also be considered to be a method of magnetic resonance imaging when the acquisition of the magnetic resonance data is also considered.

In another embodiment, the motion signal is descriptive of the breathing cycle of a subject.

In another embodiment, the magnetic resonance data is descriptive of a liver of a subject.

In another aspect, the invention provides for a computer program product comprising machine-executable instructions for execution by a processor controlling a medical imaging system. Execution of the machine-executable instructions causes the processor to receive magnetic resonance data. The magnetic resonance data comprises discrete data portions. Each data portion comprises an acquisition time and comprises a motion signal value. The discrete data portions have a sampling pattern in k-space. The sampling pattern is rotated in k-space between sequentially acquired discrete data portions. Execution of the machine-executable instructions further cause the processor to bin the discrete data portions into predetermined motion bins using the motion signal value of each of the discrete data portions. Execution of the machine-executable instructions further cause the processor to reconstruct a reference image for each of the predetermined motion bins using the binned discrete data portions.

Execution of the machine-executable instructions further cause the processor to construct a displacement vector field between a selected motion bin and each of the predetermined motion bins using the reference image for each of the predetermined motion bins. The selected motion bin is selected from the predetermined bins. Execution of the machine-executable instructions further cause the processor to bin a chosen group of the discrete data portions into a chosen time bin using the acquisition time of each of the discrete data portions.

Execution of the machine executable instructions further causes the processor to generate an enhanced image for the chosen time bin using the chosen group of the discrete data portions and the motion transform of each of the chosen group to correct the discrete data portions.

In another embodiment, execution of the machine-executable instructions further cause the processor to iteratively generate an enhanced image for the chosen time bin. The enhanced image is initially the reference image of the selected motion bin when the iterative process starts. The iterative generation of the enhanced image is performed by repeating the following for each of the discrete data portions of the chosen group. The iterative generation of the enhanced image comprises choosing a current data portion from the discrete data portions of the chosen group. The current data portion was binned into a current motion bin. The current motion bin is one of the predetermined motion bins.

The iterative process further comprises calculating a transformed image by transforming the enhanced image using the displacement vector field between the selected motion bin and the current motion bin. The iterative process further comprises transforming the transformed image into transformed k-space data. The iterative process further comprises calculating a k-space difference between k-space data of the current data portion and corresponding k-space data points of the transformed k-space data. The iterative process further comprises transforming the k-space difference into a difference image.

The iterative process further comprises transforming the difference image into a modified difference image by using an inverse of the displacement vector field between the selected motion bin and the current motion bin. The iterative process further comprises updating the enhanced image by adding the modified difference image to the enhanced image. The advantages of this computer program product have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit,"

"module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. MRF magnetic resonance data is magnetic resonance data. Magnetic resonance data is an example of medical image data. A Magnetic Resonance Imaging (MRI) image or MR image is defined herein as being the reconstructed two- or three dimensional visualization of anatomic data contained within the magnetic resonance imaging data. This visualization can be performed using a computer.

The chosen group of discrete data portions as used herein is a label which refers to discrete data portions which have been binned into a chosen time bin. The chosen time bin is a time period which can be chosen and assigns a time period or time range for the resulting enhanced image. The chosen time bin could be chosen using an algorithm or could also be received via a user interface or retrieved from a storage device.

The acquisition time of each of the discrete data portions could be assigned in different ways and can be interpreted as a time stamp assigned to the magnetic resonance data as it is acquired.

The selection of the selected motion bin and the selected time bin in the algorithms above enable the enhanced image to be generated from data that is subject to actions which happen on different time scales. For example, the subject may have been injected with a magnetic resonance contrast agent and may be breathing. The selection of the selected time bin could be used to select a time range after the contrast agent has been used contrast agent. The selected time bin could then provide time resolution of the progress of the contrast agent. The selection of the selected motion bin could be used to select a particular breathing phase. The algorithms could be applied multiple times to change the breathing phase and also the time after the contrast agent has been applied.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
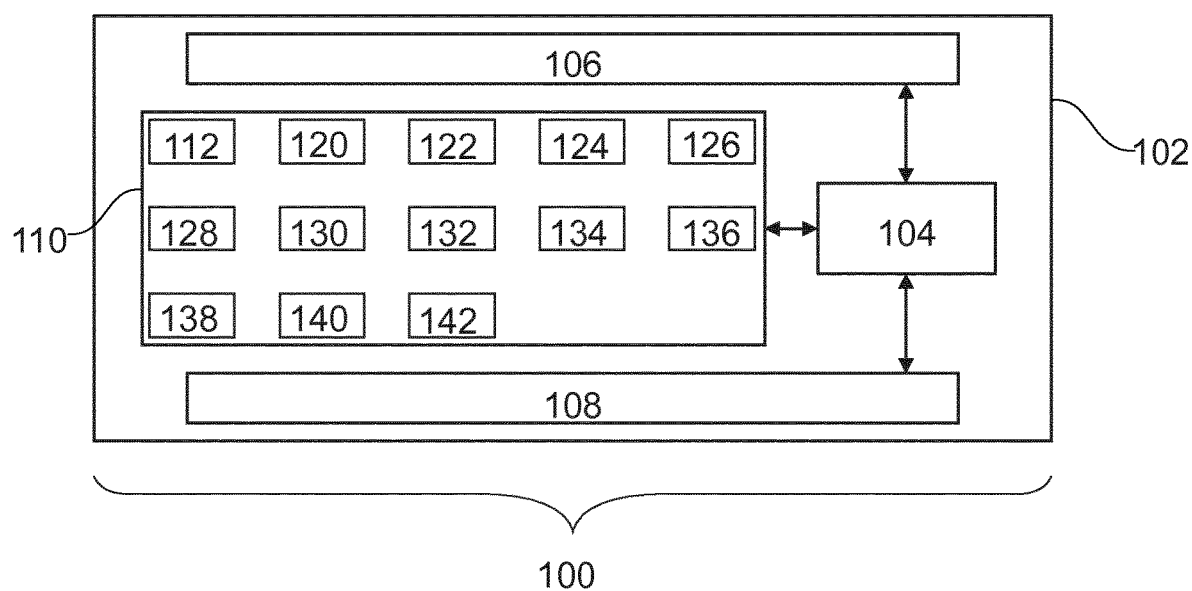
FIG. 1 illustrates an example of a medical imaging system.

FIG. 1 illustrates an example of a medical imaging system 100. The medical imaging system 100 in FIG. 1 is shown as comprising a computer 102. The computer has a processor 104. The processor is shown as being optionally connected to a hardware interface 106. The hardware interface may for example be any hardware which enables the processor 104 to either control or exchange messages with other pieces of equipment. For example, the hardware interface could be used for forming a network connection with another computer system or data network. In other examples the hardware interface 106 may be used to control other components such as a magnetic resonance imaging system. The processor 104 is also shown as being optionally connected to a user interface 108. The processor 104 is further shown as being connected to a memory 110.

The memory 110 is shown as containing machine-executable instructions 112. The machine-executable instructions 112 enable the processor 104 to perform basic functions to control the operation and function of the medical imaging system 100 and also to manipulate data and perform calculations. The memory 110 is shown as containing magnetic resonance data 120. The magnetic resonance data comprises discrete data portions. Each data portion comprises an acquisition time and comprises a motion signal value. The discrete data portions have a sampling pattern in k-space. The sampling pattern is rotated in k-space between sequentially acquired discrete data portions.

The memory 110 is further shown as containing the predetermined motion bins. The memory 110 is further shown as containing a reference image 124 for each of the predetermined motion bins 122. The memory 110 is further shown as containing a set of displacement vector fields 126 between a selected motion bin and each of the predetermined motion bins using the reference image for each of the predetermined motion bins. The memory 110 is further shown as containing a chosen time bin 128. The chosen time bin is a chosen time period into which the discrete data portions can be binned. The memory 110 is further shown as containing an enhanced image 130. The enhanced image is generated in an iterative process. At the beginning of the iteration the enhanced image is initially the reference image of the selected motion bin.

The memory 110 is further shown as containing a current data portion 132 that is being used in the iterative process. The memory 110 is further shown as containing a transformed image 134. The memory 110 is further shown as containing a transformed k-space data 136. The memory 110 is further shown as containing a k-space difference. The memory 110 is further shown as containing a difference image 140. The memory 110 is further shown as containing a modified difference image. The iterative process used to calculate the enhanced image 130 and using elements 130-142 is described below in FIG. 2.

Figure 2:
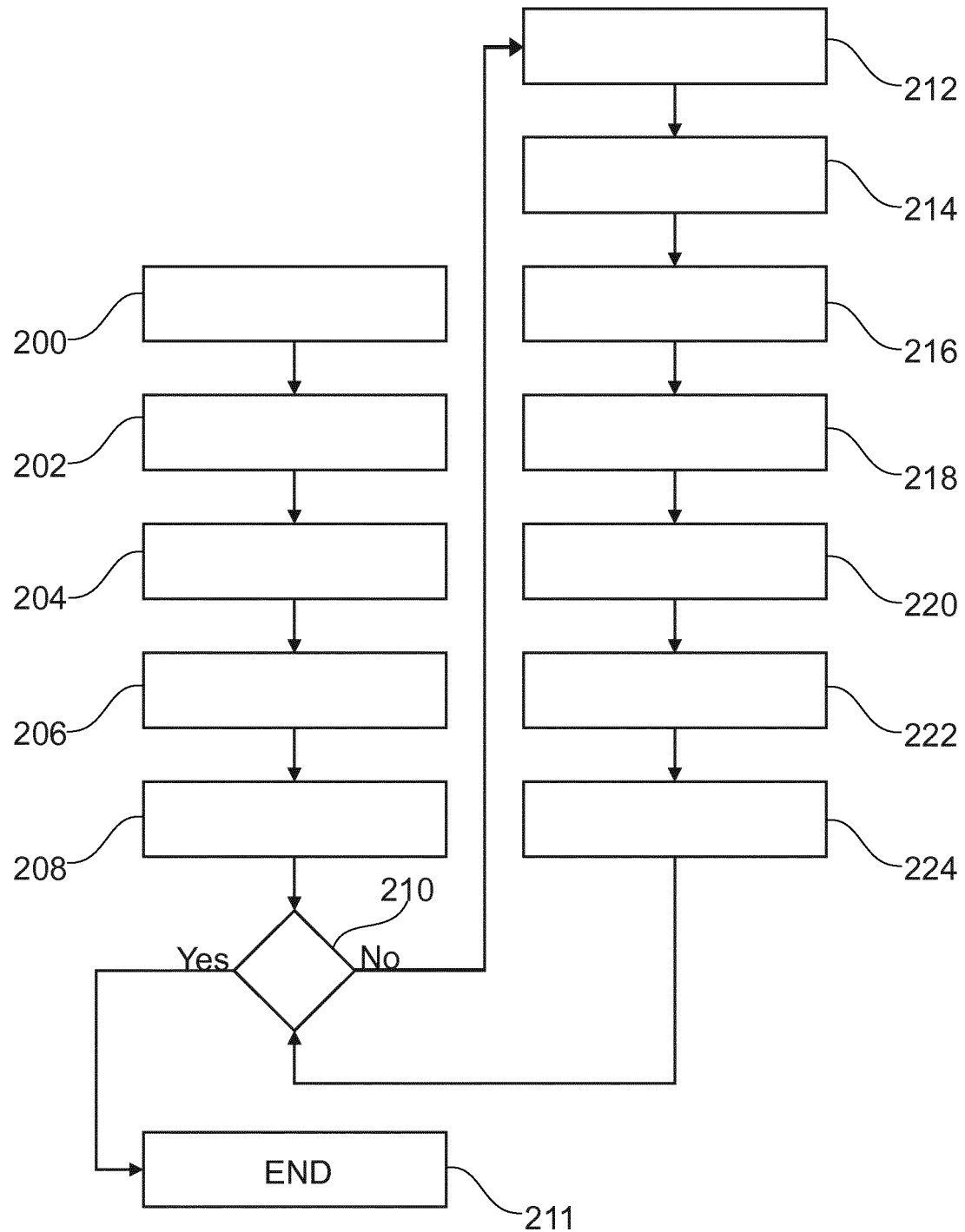
FIG. 2 shows a flow chart which illustrates a method of operating the medical imaging system of FIG. 1.

FIG. 2 shows a flowchart which illustrates a method of operating the medical imaging system 100 of FIG. 1. First in step 200 the magnetic resonance data 120 is received. The magnetic resonance data comprises discrete data portions. Each data portion comprises an acquisition time and comprises a motion signal value. The discrete data portions have a sampling pattern in k-space. The sampling pattern is rotated in k-space between sequentially acquired discrete data portions.

Next in step 202 the discrete data portions of the magnetic resonance data 120 are binned using the motion signal value of each of the discrete data portions into the predetermined motion bins 122. Next in step 204 a reference image 124 is reconstructed for each of the predetermined motion bins 122 using the bin discrete data portions within each of the predetermined motion bins. In other words, the discrete data portions contained within a particular motion bin is used to reconstruct a reference image. Next in step 206 a displacement vector field 126 is constructed between a selected motion bin and each of the predetermined motion bins 122 using the reference image 124 for each of the predetermined motion bins.

Next in step 208, a chosen group of the discrete data portions is binned into a chosen time bin 128 using the acquisition time of each of the discrete data portions. It can be seen in this Fig. that the chosen time bin and the predetermined motion bins 122 are distinct. The data for example may be copied separately into each of these bins or the bins may simply represent pointers or other indicators of which data of magnetic resonance data belongs in each particular of the predetermined motion bin 122, and the chosen time bin 128.

After step 208, the method then proceeds to step 210. Step 210 is the start of the iterative process to calculate the enhanced image 130. In the question box the condition is posed via a question which is have all of the discrete data portions of the chosen group been processed and possibly if the enhanced image has converged. If the answer is yes the method proceeds to step 211 and the method in FIG. 2 ends. If the answer is no then the method proceeds to step 212.

In step 212 a current data portion 132 is chosen from the discrete data portions of the chosen group. The current data portion was binned into a current motion bin. The current motion bin is one of the predetermined motion bins 122. Next in step 214 the transformed image 134 is calculated by transforming the enhanced image using the displacement vector field between the selected motion bins and the current motion bin. Next in step 216 the transformed image 134 is transformed into transformed k-space data. Next in step 218 a k-space difference 138 is calculated between the k-space data of the current data portion and corresponding k-space data points of the transformed k-space data. Next in step 220 the k-space difference 138 is transformed into a difference image. Then in step 222 the difference image is transformed into a modified difference image 142 using the inverse of the displacement vector field 126 between the selected motion bin and the current motion bin. Then the method proceeds to step 224. In step 224 the enhanced image is updated by adding the modified difference image to the enhanced image 130. The method then proceeds back to step 210. If all of the discrete data portions of the chosen group have been through the loop in steps 212-224 then the method may end in step 211. If not, the method proceeds to step 212 and a different current data portion is selected and the modified difference image 142 from step 224 is used when steps 212-224 are performed again.

In some implementations, the method ends after one iteration of steps 212 through 224. However, the enhanced image may not have converged in the iterative process. It may be beneficial to perform steps 212 through 224 multiple times for each discrete data portion of the chosen group. For example, the question box 210 could also include a convergence test to see if the enhanced image changes more than a predetermined amount after one cycle through the discrete data portions of the chosen group.

Figure 3:
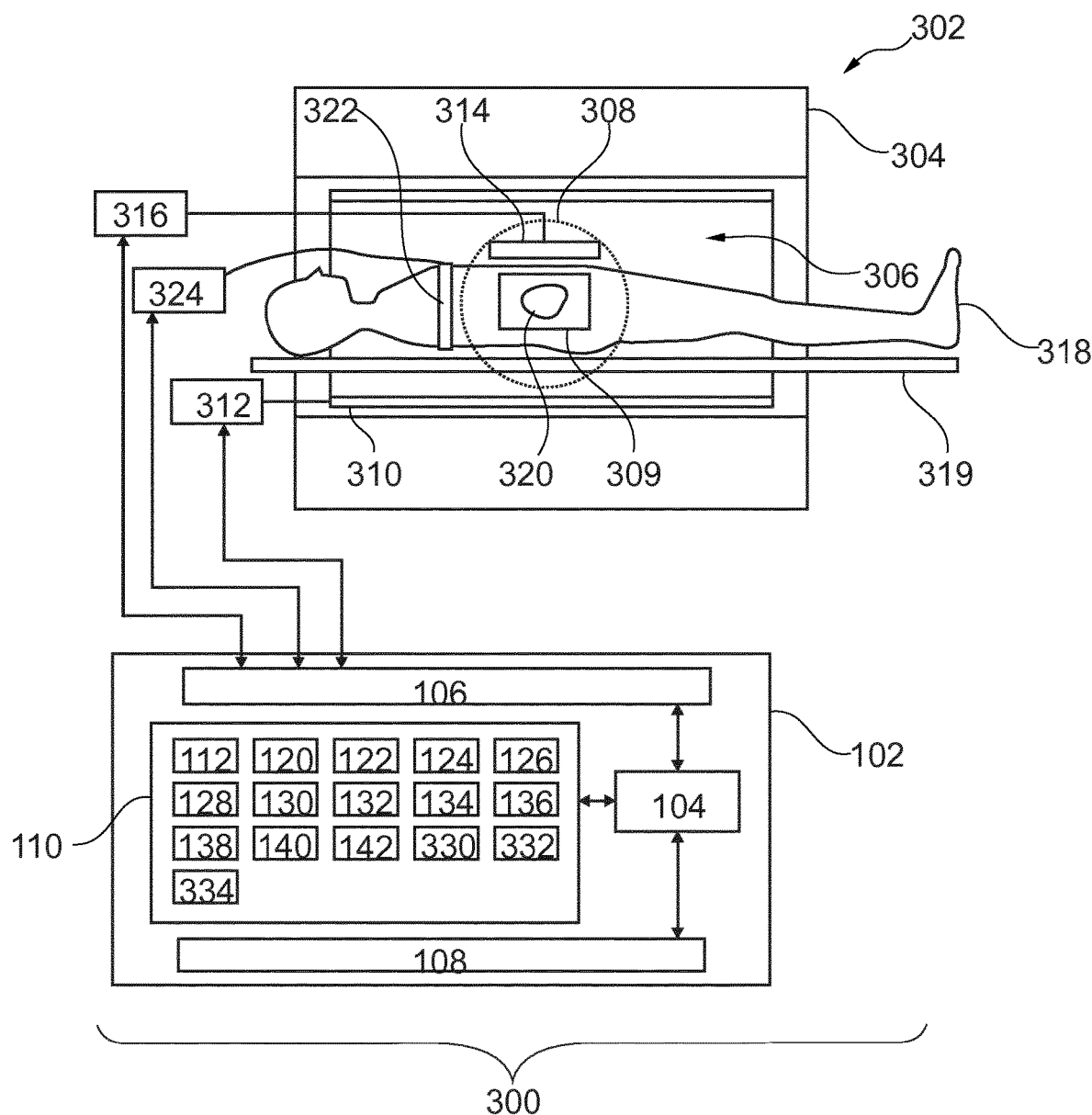
FIG. 3 illustrates a further example of a medical imaging system.

FIG. 3 illustrates a further example of a medical imaging system 300. The medical imaging system 300 depicted in FIG. 3 is similar to the medical imaging system 100 of FIG. 1. The medical imaging system 300 of FIG. 3 additionally comprises a magnetic resonance imaging system 302. The magnetic resonance imaging system 302 comprises a magnet 304, which may be cylindrical. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the magnet 304 there is an imaging zone 308 where the magnetic field is strong and uniform enough to perform magnetic resonance imaging. A region of interest 309 is shown within the imaging zone 308. Within the region of interest 309 the subject 318 has an organ 320. For example, the organ 320 could be a liver. A subject 318 is shown as being supported by a subject support 319 such that at least a portion of the subject 318 is within the imaging zone 308 and the region of interest 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Within to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the radio frequency transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The subject 318 is further shown as wearing an expansion belt 322 or respiratory belt which is able to make a signal whenever the chest of the subject 318 expands or contracts. The expansion belt 322 is shown as being connected to a subject motion detection system 324 that receives a signal from the expansion belt 322 and then sends these measurements as data via the hardware interface 106 to the processor 104. The magnetic field gradient coil power supply 312, the radio frequency transceiver 316 and the subject motion detection system 324 are all shown as being connected to the processor 104 via the hardware interface 106.

The memory 110 is further shown as containing pulse sequence commands 330. The pulse sequence commands are either commands or data which can be converted into such commands which enable the processor 104 to control the magnetic resonance imaging system 302 to acquire the magnetic resonance data 120. The memory 110 is further shown as containing motion signal values 332 and acquisition times 334 that were recorded at the same time as the magnetic resonance data 120. They may be attached to or referenced to the discrete data portions of the magnetic resonance data 120. In some instances, the motion signal values 332 and the acquisition times 334 may be appended to or associated with the discrete data portions of the magnetic resonance data 120.

Figure 4:
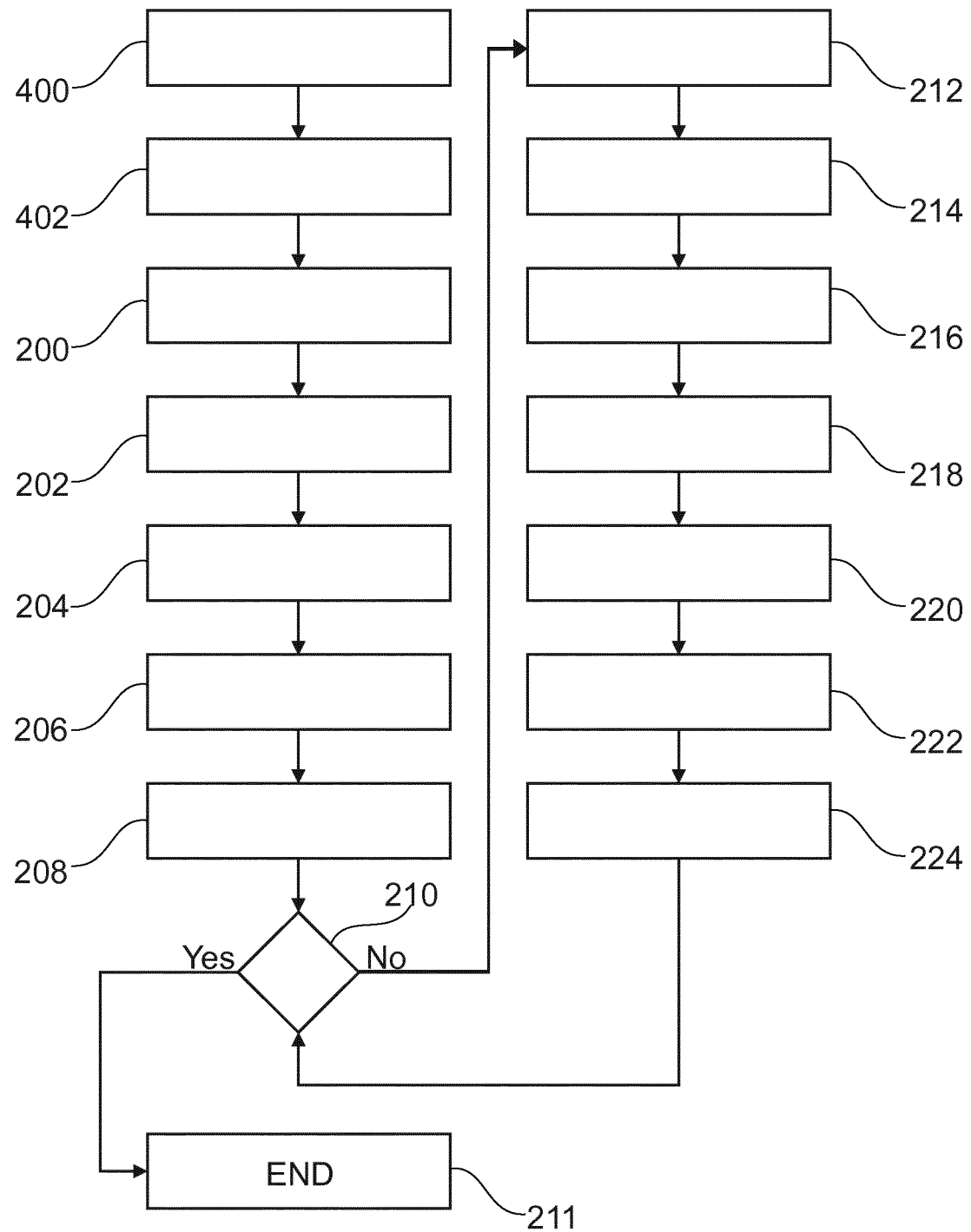
FIG. 4 shows a flow chart which illustrates a method of operating the medical imaging system of FIG. 3.

FIG. 4 shows a flowchart which illustrates a method of operating the medical imaging system 300 of FIG. 3. The method depicted in FIG. 4 is similar to the method depicted in FIG. 2. There are two additional steps. The method starts with step 400. In step 400 the magnetic resonance imaging system 302 is controlled with the pulse sequence commands 330 to acquire the magnetic resonance data 120. Next in step 402 the processor 104 controls the magnetic resonance imaging system 302 to acquire the motion signal values 332 and the acquisition times 334 at the same time as individual discrete data portions are acquired by the magnetic resonance imaging system 302. After step 402, the method proceeds to step 200 of FIG. 2.

Figure 5:
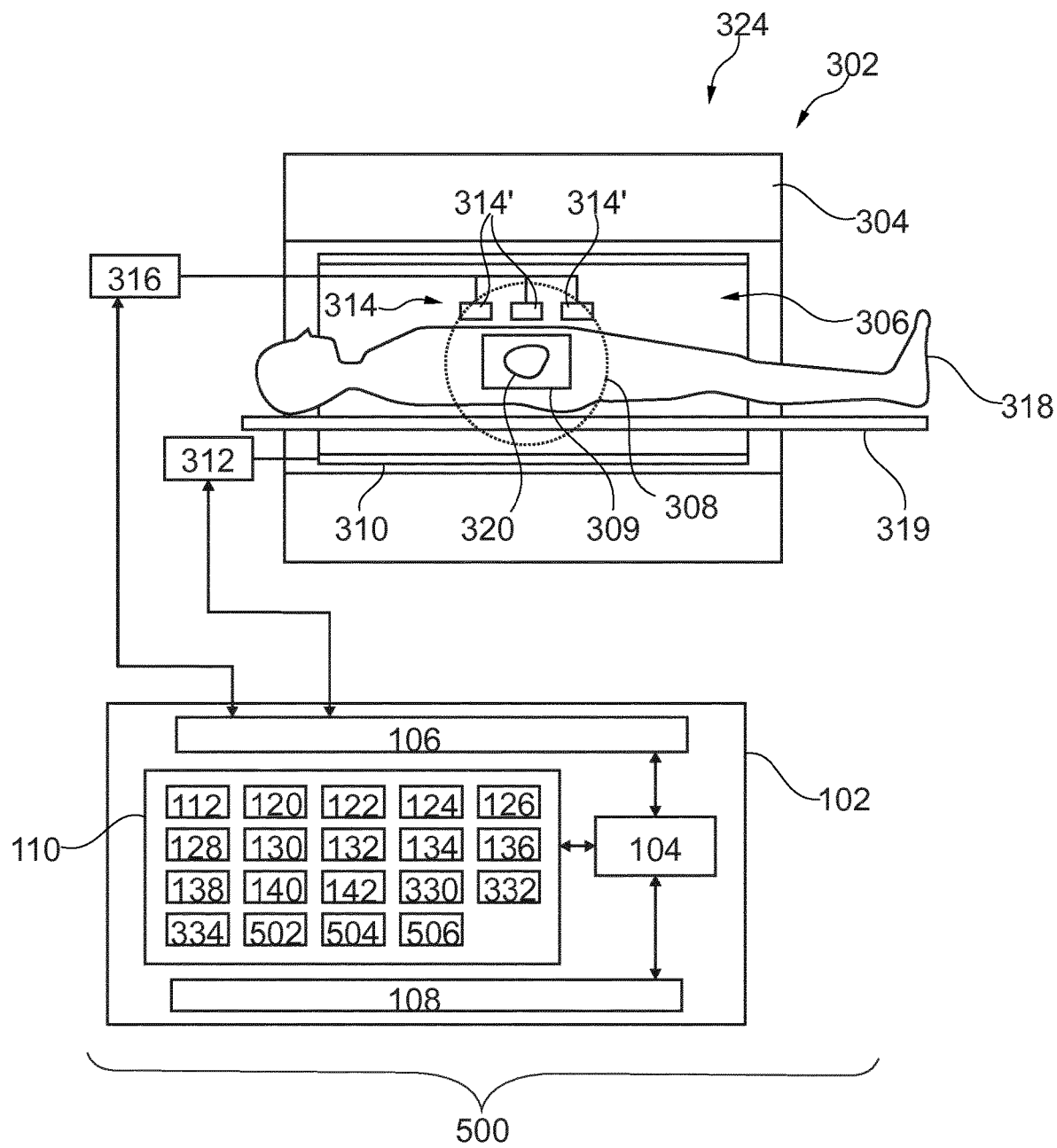
FIG. 5 illustrates a further example of a medical imaging system.

FIG. 5 illustrates a further example of the medical imaging system 500. The medical imaging system depicted in FIG. 5 is similar to the medical imaging system 300 depicted in FIG. 3 with several modifications. In this example the magnetic resonance imaging system itself functions as the subject motion detection system 324. This is achieved by the pulse sequence commands 330 acquiring navigator data 506 at the same time that the magnetic resonance data 120 is acquired. This may be performed either sequentially or the navigator data 506 may be embedded within the discrete data portions or a part of the discrete data portions. Additionally, the radio-frequency coil 314 is shown as being comprised of several separate coil elements 314'. The magnetic resonance data is recorded from each of the coil elements 314' on separate channels.

The memory 110 is further shown as containing coil sensitivity data 502 for performing parallel imaging using the magnetic resonance data 120. The coil sensitivity data 502 may be only valid for a single motion state of the subject 318. The displacement vector fields 126 may be therefore used to transform the coil sensitivity data 502 for a set of transformed of coil sensitivity data 504 for each of the predetermined motion bins 122. When dealing with data from the predetermined motion bins 122 the appropriate coil sensitivity data 502 or transform coil sensitivity data 504 is used. The memory 110 is also further shown as containing navigator data 506 for the individual discrete data portions that was derived from the magnetic resonance data 120. The motion signal values 332 may then be derived from the navigator data 506.

Examples may provide for a reconstruction method to obtain a series of images with high spatial and high temporal resolution from a golden angle, stack-of-stars dataset acquired without breath-hold. High resolution images without motion blurring are reconstructed from motion binned data. Subsequently the contrast of the DCE phase is recovered by an iterative reconstruction method, which incorporates elastic image registration and deformation to fuse acquired data at the desired contrast time to match the desired high resolution reference time image.

Dynamic contrast enhanced (DCE) MRI aims at imaging the dynamic behavior of an intravenously injected contrast agent. Especially for liver imaging there is an interest to image the arterial phase i.e. the first pass of contrast agent through the liver. This phase is too short (~5 s) to acquire enough data for a high resolution image of the liver. So a compromise between temporal and spatial resolution must be made. In addition, it is difficult to acquire data for this phase with a breath-hold scan because the timing between contrast injection and arterial phase may depend on the patient's physiology. Besides liver imaging, this technique could be relevant for: DCE imaging of other organs like breast, kidneys (a.k.a Magnetic Resonance Renography); contrast-enhanced angiography, and cardiac imaging (3D cine imaging and DCE).

One way to overcome the above-mentioned problems is to acquire data using a continuous 3D golden-angle stack-of-stars trajectory during free breathing. This sequence has the feature that any arbitrary time-segment of the data which is chosen from the entire set covers the k-space evenly and can be used to reconstruct an image of the object at the center time of the chosen time-window. The length of the time window is directly proportional to the number of profiles which are available for reconstruction. In principle, temporal and spatial resolution can be interchanged: A long time-window allows good spatial resolution, a short time-window allows good time-resolution.

However, this does not apply to free-breathing scans since choosing data from a long time-window will mix data from different respiratory motion states. As a result, the image will be blurred by motion and does not give the expected spatial resolution. To cover the arterial phase a short-time window is necessary (few radial spokes), on the other hand a certain spatial resolution is required because the features that show the contrast change are only small regions of the image. I.e., a minimum number of adjacent spokes may be selected to achieve a Nyquist radius in k-space which is large enough to cover the length scale of the features of interest (see FIG. 6 below).

In practice, this time window is so large that a significant amount of breathing motion can occur. Typically, this window will be 3 to 5 seconds long, equivalent to roughly 1-3 respiratory cycles. I.e. it is impossible to select enough profiles to depict the contrast change without being affected by breathing motion (see FIG. 7 below).

Figure 6:
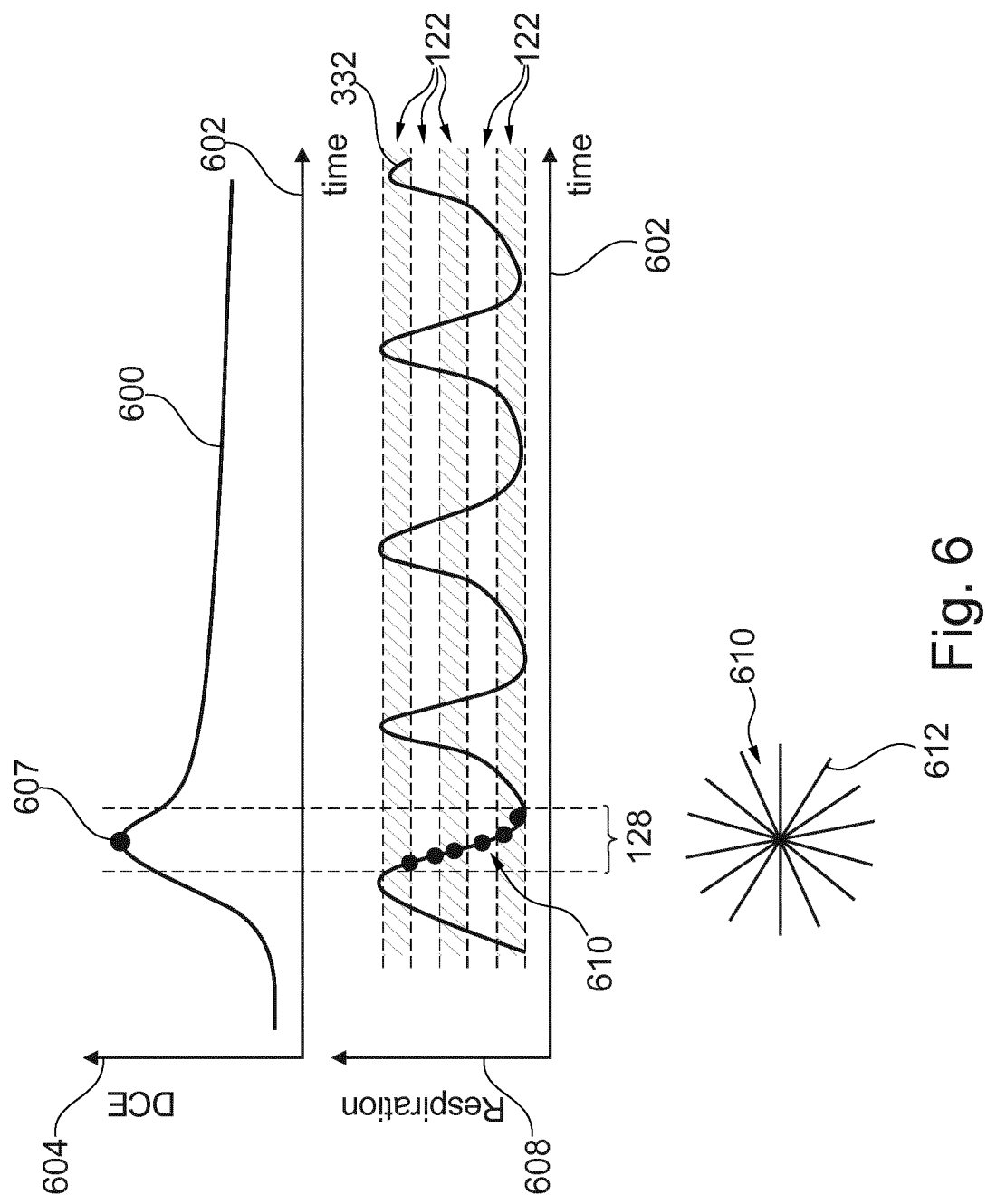
FIG. 6 illustrates the binning of discrete data portions of magnetic resonance imaging data.

FIG. 6 shows a plot which is used to explain the binning of the discrete data portions into the predetermined motion bins 122 and the chosen time bin 128. In the example shown in FIG. 6 the subject 318 of FIG. 3 or FIG. 5 has been injected with a contrast agent and the magnetic resonance imaging protocol is a dynamic contrast enhanced magnetic resonance imaging protocol. Several plots are shown in FIG. 3. The first plot 600 shows the concentration of contrast agent in the organ 320. The x-plot is time 602 versus the concentration of contrast agent 604 in the organ 320. The first plot 600 is seen as having a chosen time bin 128. Below first plot 600 is another plot of the motion signal values 332. It is a plot of time 602 versus respiratory phase 608. According to the motion signal value the discrete data portions are binned into individual predetermined motion bins 122. The discrete data portions 612 may also be binned into the chosen time bin 128. It can be seen that there is a chosen group 610 of discrete data portions 612 binned into the chosen time bin 128. The chosen time bin 128 has a central time 607. In this example, the contrast agent 600 peaks at the central time 607.

In this example, the six discrete data portions of the chosen group 610 were acquired as spokes in a 3D stack-of-stars scheme. Each line in 610 represents a sampling pattern in k-space. The spokes may be replaced by other distributions or paths such as a spiral sampling pattern.

Figure 7:
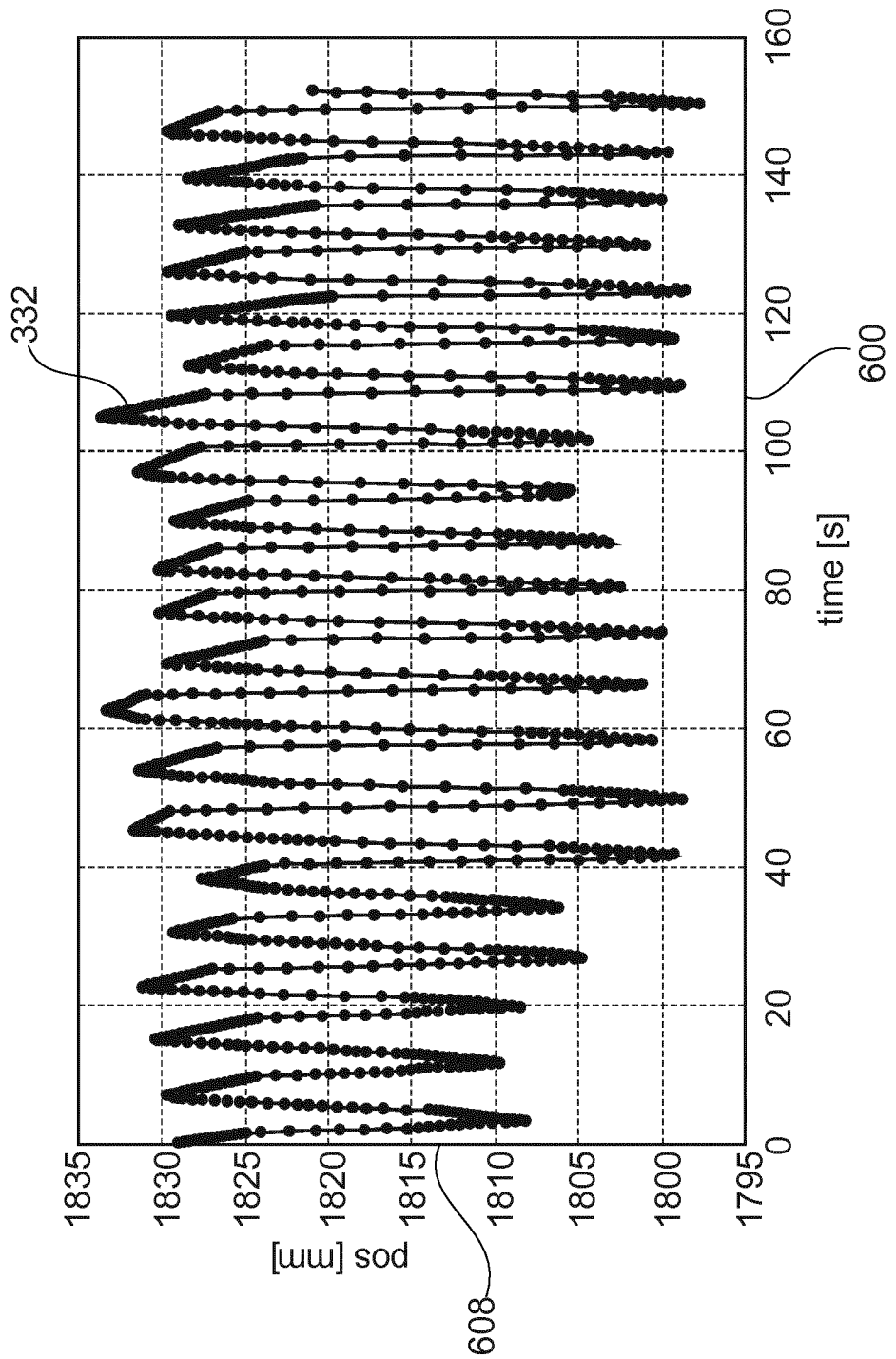
FIG. 7 shows a plot which illustrates an example of motion signal values.

FIG. 7 shows a typical movement pattern or motion signal values 332 for a free-breathing stack-of-stars liver protocol. The solid curve shows the respiratory motion, and the dots show the time points of data acquisition. This shows that it may be difficult for time points during inspiration or expiration to select a continuous time window which is not affected by respiratory motion. The binning scheme illustrated in FIG. 6 however will work.

Examples may provide for a reconstruction method which uses motion compensation to fuse the contrast information from adjacent spokes into a single motion compensated image which represents the motion state at the center of the selected time-window. In this way, a high-temporal and high-spatial resolution can be obtained.

A first step is to reconstruct a series of high resolution images which depict the respiratory motion (ignoring contrast changes).

Second step is to determine displacement vector fields (DVFs) between these motion states.

Third and final step is to produce an image for a selected time-point which displays the contrast at the chosen time-point. To this end, a time-window is selected around the chosen point and a motion compensated, iterative reconstruction fuses all data from this time-window into a single image representing the motion state from the center of the window. The algorithm eliminates the influence of respiratory motion by using the estimated DVFs to deform the current image into the motion state of the spoke which is currently processed inside the iteration loop.

This may enable reconstructing a series of high resolution images showing contrast agent dynamics and respiratory motion at the same time. As an option, it is possible to choose a single respiratory state as reference and produce a series of high resolution images which only show contrast agent dynamics.

In some examples, a respiratory navigator signal is used to assign a respiratory phase to each of the acquired time-points. This navigator signal can be obtained in a number of known ways:
  from the data itself by self-navigation (e.g. projection along z-axis),
  interleaving a MR navigator into the sequence,
  a respiratory belt,
  vital-signs camera or other breathing sensors.

The motion range during breathing may be divided into a number of respiratory bins with a certain width. All data within a bin are used to reconstruct one high-resolution image per bin. Since these data are from the whole scan duration, no information on contrast agent dynamics is visible but high spatial resolution is possible since the number of radial spokes in each bin is typically large.

The DVFs can be estimated by applying a registration algorithm, preferably an elastic registration (e.g. the FEIR algorithm, see for example S Kabus and C Lorenz. Fast elastic image registration. In Medical Image Analysis For The Clinic—A Grand Challenge, pages 81-89, 2010). These DVFs can be used to deform each of the high-resolution images for the respiratory bins into one another (and into intermediate states by applying appropriate fractions of the DVF). I.e. using the DVFs it is possible to deform an image from a given reference time-point to the respiratory state of each time-point in the data acquisition.

Figure 8:
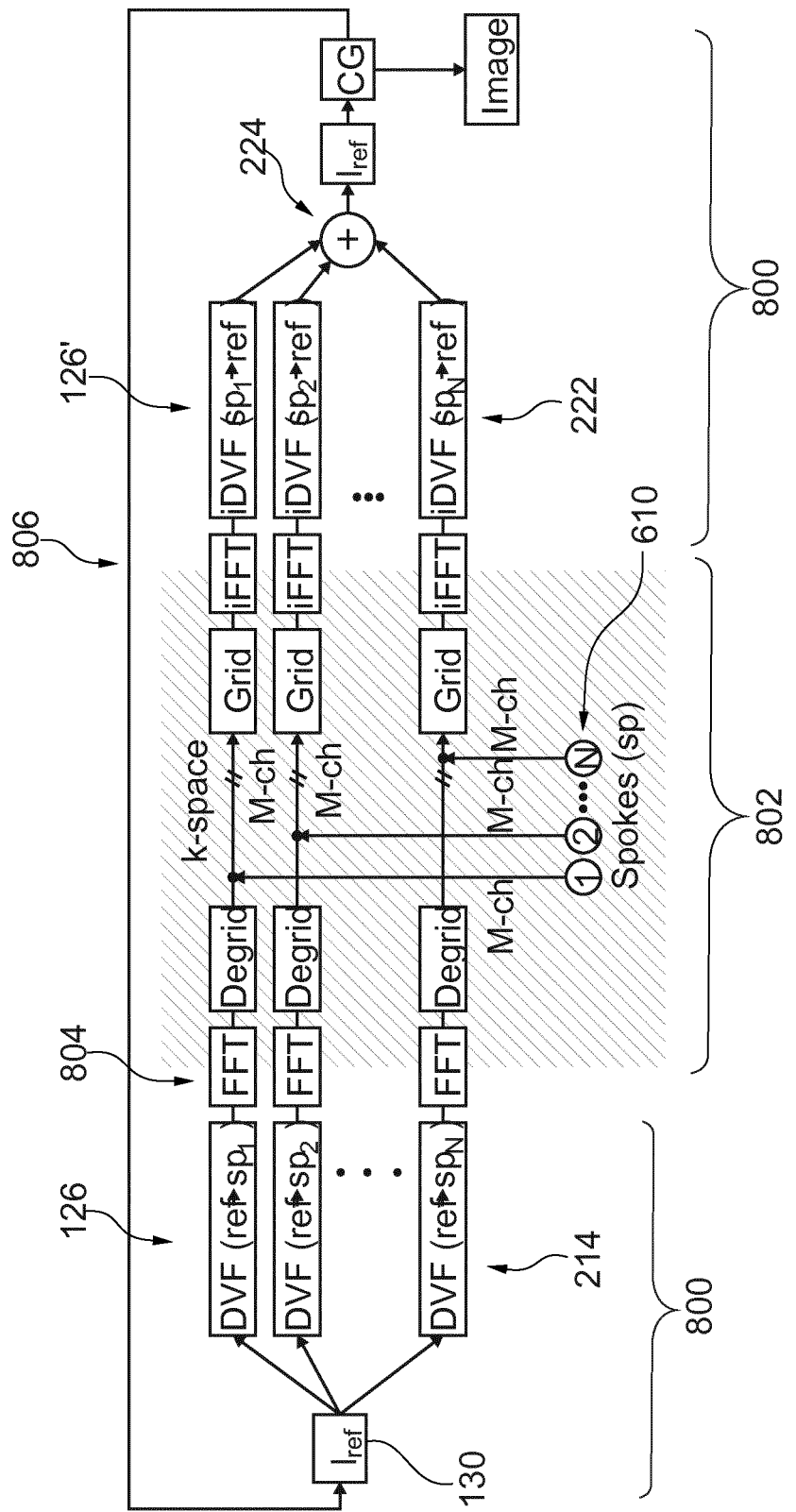
FIG. 8 shows a flow chart which illustrates a method according to an example.

One way to achieve a motion compensated reconstruction of all data within a certain time-window is described in the following (a flow-graph of the method is shown in FIG. 8 below):

The iterative reconstruction is initialized with the high-resolution image which corresponds to the center of the chosen time-window. In the iteration loop the following steps are executed:
  choose a spoke from the selected time-window
  deform the current image into the motion state of the chosen spoke
  transform the image to k-space (one for each coil element)

compute the difference to the measured data of the selected spoke transform the differences into image space and combine the information from the different channels apply the inverse DVF to the image of combined differences add the difference to the (untransformed) current image and use this image as the new "current image" for the next iteration.

The result of this algorithm is a high-resolution image which contains the contrast information of the selected time-window The description above outlines the basic idea of the algorithm. Variations of this scheme are possible, e.g. including spatial or temporal regularization terms, weighting data with temporal distance to the center of the time-window, applying DVFs to the coil sensitivity maps which are used in the iteration loop, using auto-calibration to estimate coil sensitivity maps for each motion state, reducing the spatial resolution in the iteration loop to speed up iterations.

Modifications to the above described algorithm can be made. Instead of deforming the difference image and adding it to the untransformed image, you can first add the difference to the (deformed) current image and then transform the result back to the original motion state.

The whole iteration could possibly be improved if the deformation at the end of the current iteration and the deformation at the beginning of the next iteration are combined into a single step by summing the two DVFs which are involved.

Advantages of this combination may include:

1. One may save some time because only one instead of two deformations must be executed.
2. The amount of blurring of the images may possibly be reduced because the deformation might involve some interpolation on the image data which reduces the sharpness.

FIG. 8 shows a description of the iterative calculation of the enhanced image. The algorithm depicted in FIG. 8 is divided into parts which are performed in image space 800 and performed in k-space 802. To transform between image space 800 and k-space 802 a Fourier transform 804 is performed. To transform back again from k-space 802 to image space 800 an inverse Fourier transform 806 is performed. Each of the horizontal lines in the algorithm of FIG. 8 represents the processing of one of the chosen group 610 which are within the chosen time bin 606. The algorithm in FIG. 6 starts with the reference image of the selected motion bin 606.

FIG. 8 shows a flow graph of an iterative reconstruction using N spokes and M channels. Operations carried out in k-space are indicated by the region of grey background.

The processing scheme from above can also be applied to non-contrast free breathing acquisitions to achieve a motion compensated high-resolution image (e.g. a 3D stack-of-stars scan for liver imaging). In this case the entire scan is shorter and the respiratory bins will contain fewer data i.e. the spatial resolution of the respiratory bins will be lower than the maximum achievable resolution. Still DVFs can be computed by registration. The iterative reconstruction scheme from above can now be used to compute a single motion compensated, high-resolution image from the entire scan data. I.e. only a single time-window is used which comprises all data.

Figure 9:
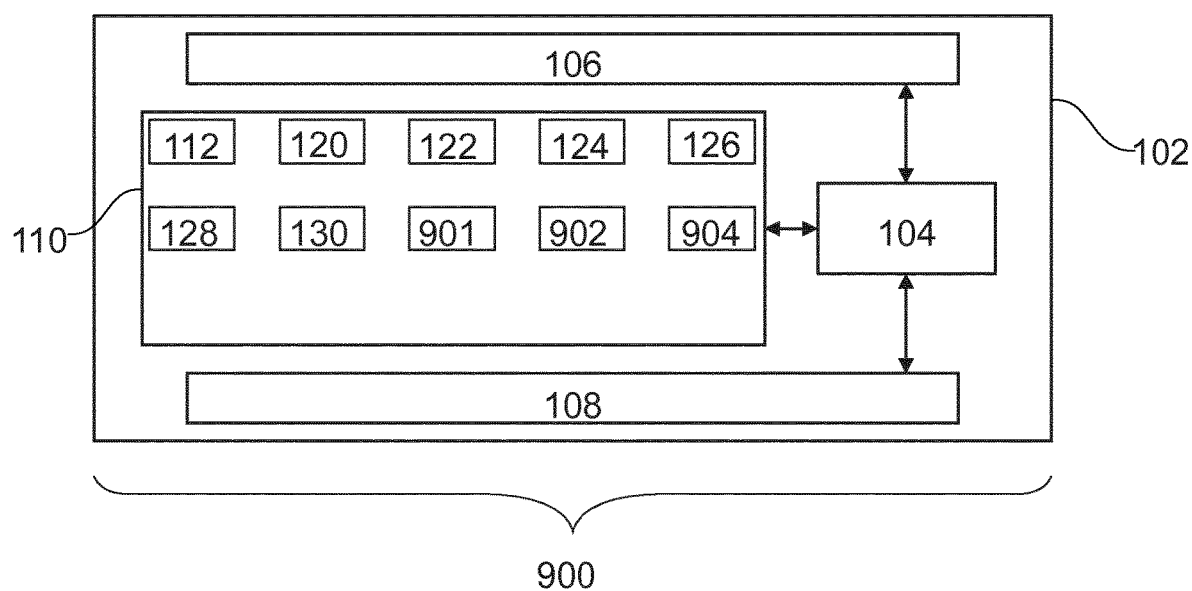
FIG. 9 illustrates a further example of a medical imaging system.

FIG. 9 illustrates a further example of a medical imaging system 900. The medical imaging system 900 in FIG. 9 is similar to the medical imaging system 100 in FIG. 1 except that in FIG. 9 the generation of an enhanced image is performed by transforming k-space data directly within k-space and then after the k-space has been combined reconstructing the enhanced image. The memory 110 does not contain elements 132, 134, 136, 138, 140, or 142 from FIG. 1. Instead the memory 110 is shown as further containing transformed k-space data 901 that was calculated by transforming each of the discrete data portions 612 of the chosen group 610 using its motion transform 904. The motion transform in image space has been transformed into a motion transform 904 in k-space. The memory 110 is further shown as containing combined k-space data 902 that was generated by combining the k-space data of the selected motion bin with the transformed k-space data 901 of each of the discreet data portions. The enhanced image 130 is then reconstructed from the combined k-space data 902.

Figure 10:
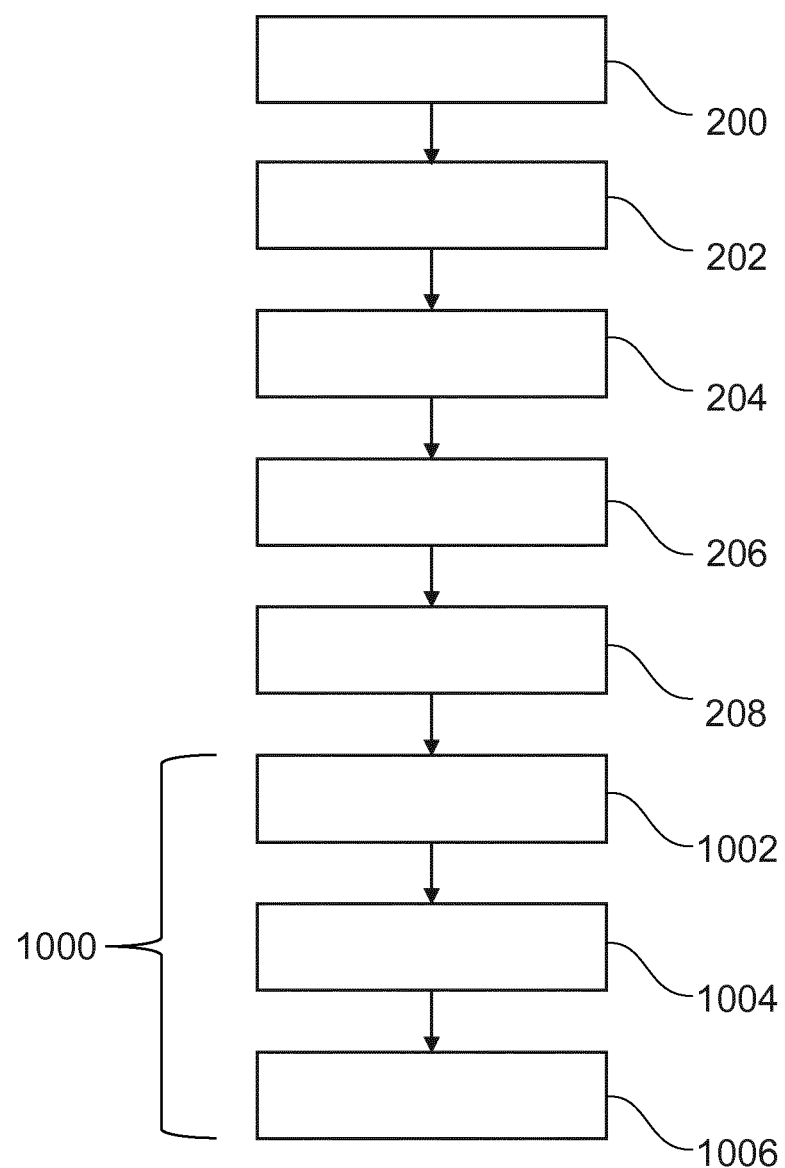
FIG. 10 shows a flow chart which illustrates a method of operating the medical imaging system of FIG. 9.

FIG. 10 shows a flowchart which illustrates a method of operating the medical imaging system 900 of FIG. 9. The method in FIG. 10 is similar to the method illustrated in FIG. 2. Steps 200, 202, 204, 206, and 208 are identical with the method steps performed in FIG. 2. After step 208 the method then proceeds to step 1000 where the enhanced image 130 is generated for the chosen time bin using the chosen group of discreet data portions and the motion transform of each of the chosen group to correct the discreet data portions. Step 1000 may be performed in several different ways. Steps 210, 211, 212, 214, 216, 218, 220, 222 and 224 in FIG. 2 correspond to step 1000. In FIG. 10 an alternative to the method in FIG. 2 is presented where the enhanced image 130 is calculated using k-space and is not iterative. For this step 1000 comprises the sub-steps 1002, 1004, and 1006. In step 1002 transformed k-space data 901 is calculated by transforming each of the discreet data portions of the chosen group using its motion transform. Then in step 1004 the combined k-space data is generated by combining k-space data of the selected motion bin with the transformed k-space data 901 of each of the discreet data portions. Finally, in step 1006 the enhanced image 130 is reconstructed from the corrected combined k-space data 902. The method of FIG. 10 can be used to reconstruct the enhanced image for the medical instruments illustrated in FIGS. 3 and 5. In the above k-space version of the algorithm (FIG. 10), iteration is not required between image and k-space. Instead, it may generate a 3D k-space from a mixture of the reference image for the motion bin (transformed into k-space) and the (motion compensated) data from the chosen time bin.

In detail:

The center of the chosen time bin may belong to a certain motion state. The reference image of this motion state can be used to compute a fully sampled, multi-channel, 3D k-space for this motion state (by multiplication with coil sensitivities followed by Fourier-transform). (This corresponds to initializing the iteration with the reference image.) Now data on points which were sampled during the selected time bin are replaced by the data which were actually acquired during the selected time bin. If the data point belongs to a different motion state, the data are compensated for the difference between both motion states before the replacement.

Since this motion compensation is performed in k-space, only rigid motions can be compensated by applying appropriated phase shifts and rotations to the sampled data.

Finally, the enhanced image for the chosen time bin is reconstructed from the combined 3D k-space data by Fourier-transformation and channel-combination.

The above scheme uses a hard-gating window in time: k-space positions outside the selected time window are taken from the transformed reference image and k-space positions inside the time window are fully replaced by the acquired data.

This can be generalized to a situation where the time window is defined by a continuous function between 0 and 1: The combined dataset is then formed as a weighted sum of data from the transformed reference image and the acquired data where the weight is given by the gating window function.

One advantage of the k-space version of the algorithm when compared to the image-space version is that it is much faster because no iteration between k-space and image space is required.

Some consequences of the k-space version of the algorithm include:

The motion compensation cannot correct the influence of a changing coil sensitivity map (CSM) which occurs if there is substantial motion relative to the coil.

It is limited to rigid motion only (and even this not fully exact because of the CSM issues).

The methods reconstruct a reference image from the data of each motion bin. The rotating k-space pattern inherently oversamples central k-space, which enables reconstructing a low-resolution image for each motion bin. But reconstruction of a reference image is also possible for data acquired with Cartesian sampling pattern:

Motion binning may result in an irregular data distribution for the datasets belonging to each motion state. However, compressed sensing image reconstruction can be employed to reconstruct an image for each motion bin from these irregularly sampled k-space data, provided the data density in central k-space is sufficiently high.

One way to ensure this is to acquire data on a certain k-space position not only once but multiple times during the entire data acquisition period (oversampling). Simply acquiring all data points n-times may be inefficient because it increases the scan time by a factor of n.

A more efficient oversampling strategy can be designed if there is some prior knowledge on the time spent in each motion state (e.g. average breathing pattern, heart-rate . . . ). Then the oversampling pattern can be optimized to generate a certain data density in k-space after motion binning with high probability.

If the motion signal determining the binning is available in real-time, it is possible to adapt the oversampling pattern in real-time according to the current filling state of the k-space for each motion bin.

Another option to increase the amount of data in k-space for reconstruction of the reference image of each motion bin is to fill gaps in k-space by data from adjacent motion bins (possibly weighted down with a factor depending on the difference in motion state). This option is less preferred because it mixes data from different motion states, and thus might lead to reference images corrupted by motion artifacts. This option may still be useful for motion states with very low data density where the reference image is heavily corrupted by sub-sampling artifacts if no data from other motion bins are used.

Various embodiments may possibly be described by one or more of the following features specified in the following numbered clauses:

1. A feature of a medical imaging system (100, 300, 500) comprising:
   a memory (110) storing machine executable instructions (112);
   a processor (104) for controlling the medical imaging system, wherein execution of the machine executable instructions causes the processor to:
   receive (200) magnetic resonance data (120), wherein the magnetic resonance data comprises discrete data portions (612), wherein each data portion comprises an acquisition time and comprises a motion signal value (332), wherein the discrete data portions have a sampling pattern in k-space, wherein the sampling pattern is rotated in k-space between sequentially acquired discrete data portions;
   bin (202) the discrete data portions into predetermined motion bins (122) using the motion signal value of each of the discrete data portions;
   reconstruct (204) a reference image (124) for each of the predetermined motion bins using the binned discrete data portions;
   construct (206) a displacement vector field (126) between a selected motion bin and each of the predetermined motion bins using the reference image for each of the predetermined motion bins, wherein the selected motion bin is selected from the predetermined motion bins;
   bin (208) a chosen group (610) of the discrete data portions into a chosen time bin (128) using the acquisition time of each of the discrete data portions;
   wherein execution of the machine executable instructions further causes the processor to iteratively generate an enhanced image (130) for the chosen time bin, wherein the enhanced image is initially the reference image of the selected motion bin, wherein the iterative generation of the enhanced image is performed by repeating the following for each of the discrete data portions of the chosen group:
   choosing (212) a current data portion (132) from the discrete data portions of the chosen group, wherein the current data portion was binned into a current motion bin, wherein the current motion bin is one of the predetermined motion bins;
   calculating (214) a transformed image (134) by transforming the enhanced image using the displacement vector field between the selected motion bin and the current motion bin;
   transforming (216) the transformed image into transformed k-space data (136);
   calculating (218) a k-space difference (138) between k-space data of the current data portion and corresponding k-space data points of the transformed k-space data;
   transforming (210) the k-space difference into a difference image (140);
   transforming (212) the difference image into a modified difference image (142) by using an inverse of the displacement vector field between the selected motion bin and the current motion bin; and
   updating (214) the enhanced image by adding the modified difference image to the enhanced image.

2. The medical imaging system of clause 1, wherein the medical imaging system further comprises a magnetic resonance imaging system (302), wherein the medical imaging system further comprises a subject motion detection system (324) configured for measuring the motion signal value, wherein the memory further contains pulse sequence commands (330), wherein the pulse sequence commands are configured for acquiring the magnetic resonance data according to a continuous sampling magnetic resonance protocol, wherein execution of the machine executable instructions further cause the processor to:

control (400) the magnetic resonance imaging system with the pulse sequence commands to acquire the magnetic resonance data; and control (402) the magnetic resonance imaging system to acquire the motion signal during or sequential to acquisition of the magnetic resonance data.

3. The medical imaging system of clause 2, wherein the subject motion detection system comprises the magnetic resonance imaging system, wherein the pulse sequence commands are adapted for acquiring magnetic resonance navigator data during or sequential to the acquisition of the magnetic resonance data, wherein execution of the machine executable instructions further cause the processor to calculate the motion signal at least partially using the magnetic resonance navigator data.

4. The medical imaging system of clause 2 or 3, wherein the continuous sampling magnetic resonance protocol is a dynamic contrast enhanced magnetic resonance imaging protocol.

5. The medical imaging system of any one of clauses 2 through 4, wherein the subject motion detection system comprises any one of the following: a cardiac motion detector, an ECG, a VCG, a pulseoximeter, a respiratory belt (322), a breath sensor, an optical motion detector, a camera system, a 3D camera system, an optical fiducial marker detector system, a magnetic resonance fiducial maker detector system, and combinations thereof.

6. The medical imaging system of any one of the preceding clauses, wherein the magnetic resonance data is parallel imaging magnetic resonance data, wherein the difference image incorporates k-space differences from multiple magnetic resonance coil elements.

7. The medical imaging system of clause 6, wherein the memory contains coil sensitivity data (502), wherein execution of the machine executable instructions further causes the processor to correct the reference image for each of the predetermined motion bins by correcting the coil sensitivity data using the vector displacement fields.

8. The medical imaging system of clause 6, wherein execution of the machine executable instructions further causes the processor to acquire coil sensitivity data for each of the predetermined motion bins, and wherein the reference image for each of the predetermined motion bins is calculated using its coil sensitivity data.

9. The medical imaging system of any one of the preceding clauses, wherein execution of the machine executable instructions further causes the processor to bin the discrete data portions into predetermined time bins, wherein execution of the machine executable instructions further causes the processor to iteratively generate the enhanced image for each of the predetermined time bins by setting the chosen time bin to each of the predetermined temporal bins.

10. The medical imaging system of clause 9, wherein any one of the following:

the reference image for initializing the enhanced image for each of the predetermined time bins is identical; and execution of the machine executable instructions causes the processor to transform the reference image for each of the predetermined time bins to a common motion state using the displacement vector fields.

11. The medical imaging system of any one of the preceding clauses, wherein execution of the machine executable instructions further causes the processor to calculate an elastic registration for the reference image of each of the predetermined motion bins, and wherein the displacement vector field is interpolated for each current data portion using the elastic registration.

12. The medical imaging system of any one of the preceding clauses, wherein the chosen time bin has a central time, wherein the k-space difference is weighted by a weighting factor dependent upon a time difference between the central time and the acquisition time of the current data portion, wherein as the time difference decreases the weighting factor increases.

13. The medical imaging system of any one of the preceding clauses, the sampling pattern in k-space of the discrete data portions is any one of the following:

a spiral trajectory; and a linear trajectory.

14. A feature of a method of image processing, wherein the method comprises:

receiving (200) magnetic resonance data, wherein the magnetic resonance data comprises discrete data portions, wherein each data portion comprises an acquisition time and comprises a motion signal value, wherein the discrete data portions have a sampling pattern in k-space, wherein the sampling pattern is rotated in k-space between sequentially acquired discrete data portions;

binning (202) the discrete data portions into predetermined motion bins using the motion signal value of each of the discrete data portions;

reconstructing (204) a reference image for each of the predetermined motion bins using the binned discrete data portions;

constructing (206) a displacement vector field between a selected motion bin and each of the predetermined motion bins using the reference image for each of the predetermined motion bins, wherein the selected motion bin is selected from the predetermined motion bins;

binning (208) a chosen group of the discrete data portions into a chosen time bin using the acquisition time of each of the discrete data portions;

wherein execution of the machine executable instructions further causes the processor to iteratively generate an enhanced image for the chosen time bin, wherein the enhanced image is initially the reference image of the selected motion bin, wherein the iterative generation of the enhanced image is performed by repeating the following for each of the discrete data portions of the chosen group:

choosing (212) a current data portion from the discrete data portions of the chosen group, wherein the current data portion was binned into a current motion bin, wherein the current motion bin is one of the predetermined motion bins;

calculating (214) a transformed image by transforming the enhanced image using the displacement vector field between the selected motion bin and the current motion bin;

transforming (216) the transformed image into transformed k-space data;

calculating (218) a k-space difference between k-space data of the current data portion and corresponding k-space data points of the transformed k-space data;

transforming (210) the k-space difference into a difference image;

transforming (212) the difference image into a modified difference image by using an inverse of the displacement vector field between the selected motion bin and the current motion bin; and updating (214) the enhanced image by adding the modified difference image to the enhanced image.

15. A feature of a computer program product comprising machine executable instructions for execution by a processor controlling a medical imaging system, wherein execution of the machine executable instructions causes the processor to:
- receive (200) magnetic resonance data, wherein the magnetic resonance data comprises discrete data portions, wherein each data portion comprises an acquisition time and comprises a motion signal value, wherein the discrete data portions have a sampling pattern in k-space, wherein the sampling pattern is rotated in k-space between sequentially acquired discrete data portions;
- bin (202) the discrete data portions into predetermined motion bins using the motion signal value of each of the discrete data portions;
- reconstruct (204) a reference image for each of the predetermined motion bins using the binned discrete data portions;
- construct (206) a displacement vector field between a selected motion bin and each of the predetermined motion bins using the reference image for each of the predetermined motion bins, wherein the selected motion bin is selected from the predetermined motion bins;
- bin (208) a chosen group of the discrete data portions into a chosen time bin using the acquisition time of each of the discrete data portions;

wherein execution of the machine executable processors causes the processor to iteratively generate an enhanced image for the chosen time bin, wherein the enhanced image is initially the reference image of the selected motion bin, wherein the iterative generation of the enhanced image is performed by repeating the following for each of the discrete data portions of the chosen group:
- choosing (212) a current data portion from the discrete data portions of the chosen group, wherein the current data portion was binned into a current motion bin, wherein the current motion bin is one of the predetermined motion bins;
- calculating (214) a transformed image by transforming the enhanced image using the displacement vector field between the selected motion bin and the current motion bin;
- transforming (216) the transformed image into transformed k-space data;
- calculating (218) a k-space difference between k-space data of the current data portion and corresponding k-space data points of the transformed k-space data;
- transforming (220) the k-space difference into a difference image;
- transforming (222) the difference image into a modified difference image by using an inverse of the displacement vector field between the selected motion bin and the current motion bin; and
- updating (224) the enhanced image by adding the modified difference image to the enhanced image.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical imaging system
102 computer
104 processor
106 hardware interface
108 user interface
110 memory
112 machine executable instructions
120 magnetic resonance data
122 predetermined motion bins
124 reference images
126 motion transform or displacement vector fields
126' inverse displacement vector fields
128 chosen time bin
130 enhanced image
132 current data portion
134 transformed image
136 transformed k-space data
138 k-space difference
140 difference image
142 modified difference image
200 receive magnetic resonance data
202 bin the discrete data portions into predetermined motion bins using the motion signal value of each of the discrete data portions
204 reconstruct a reference image for each of the predetermined motion bins using the binned discrete data portions
206 construct a displacement vector field between a selected motion bin and each of the predetermined motion bins using the reference image for each of the predetermined motion bins, wherein the selected motion bin is selected from the predetermined motion bins
208 bin a chosen group of the discrete data portions into a chosen time bin using the acquisition time of each of the discrete data portions
210 Have all diescrete data portions of the chosen group been processed?
212 choosing a current data portion from the discrete data portions of the chosen group
214 calculating a transformed image by transforming the enhanced image using the displacement vector field between the selected motion bin and the current motion bin
216 transforming the transformed image into transformed k-space data
218 calculating a k-space difference between k-space data of the current data portion and corresponding k-space data points of the transformed k-space data
210 transforming the k-space difference into a difference image 212 transforming the difference image into a modified difference image by using an inverse of the displacement vector field between the selected motion bin and the current motion bin
214 updating the enhanced image by adding the modified difference image to the enhanced image
300 medical imaging system
302 magnetic resonance imaging system
304 magnet
306 bore of magnet
308 imaging zone
309 region of interest
310 magnetic field gradient coils
312 magnetic field gradient coil power supply
314 radio-frequency coil
314' coil elements
316 transceiver
318 subject
319 subject support
320 organ
322 expansion belt or respiratory belt
324 subject motion detection system
330 pulse sequence commands
332 motion signal values
334 acquistion times
400 control the magnetic resonance imaging system with the pulse sequence commands to acquire the magnetic resonance data
402 control the magnetic resonance imaging system to acquire the motion signal during or sequential to acquisition of the magnetic resonance data
500 medical imaging system
502 coil sensitivity data
504 transformed coil sensitivity data
506 navigator data
600 plot of contrast agent in organ
602 time
604 concentration of contrast agent in organ
607 central time
608 respiratory phase
610 chosen group
612 discrete data portion
800 image space
802 k-space
804 Fourier transform
806 inverse Fourier transform
900 medical imaging system
901 transformed k-space data
902 combined k-space data
904 motion transform
1000 generate an enhanced image for the chosen time bin using the chosen group of the discrete data portions and the motion transform of each of the chosen group to correct the discrete data portions
1002 calculating transformed k-space data by transforming of each of the discrete data portions of the chosen group using its motion transform
1004 generate combined k-space data by combining k-space data of the selected motion bin with the transfomred k-space data of each of the discrete data portions
1006 reconstructing the enhanced image from the corrected k-space data

The invention claimed is:
1. A medical imaging system comprising:
a processor;
a tangible non-transitory computer readable medium that stores machine executable instructions, which when executed by the processor,
causes the processor to:
receive magnetic resonance data, wherein the magnetic resonance data comprises discrete data portions, wherein each data portion comprises an acquisition time and comprises a motion signal value, wherein the discrete data portions have a sampling pattern in k-space;
bin the discrete data portions into predetermined motion bins using the motion signal value of each of the discrete data portions, forming binned discrete data portions;
reconstruct a reference image for each of the predetermined motion bins using the binned discrete data portions;
construct a motion transform between a selected motion bin and each of the predetermined motion bins using the reference image for each of the predetermined motion bins, wherein the selected motion bin is selected from the predetermined motion bins, forming a plurality of corresponding motion transforms;
bin a chosen group of the discrete data portions into a chosen time bin using the acquisition time of each of the discrete data portions; and
generate an enhanced image for the chosen time bin using the chosen group of the discrete data portions and the motion transform of each of the discrete data portions of the chosen group to correct the discrete data portions, wherein the enhanced image is initially the reference image of the selected motion bin and iterative generation of the enhanced image is performed by execution of the machine executable instructions repeatedly by the processor that cause the processor, for each of the discrete data portions of the chosen group, to:
choose a current data portion from the discrete data portions of the chosen group, wherein the current data portion is binned into a current motion in, wherein the current motion bin is one of the predetermined motion bins;
calculate a transformed image by transforming the enhanced image using the motion transform between the selected motion bin and the current motion bin;
transform the transformed image into transformed k-space data;
calculate a k-space difference between k-space data of the current data portion and corresponding k-space data points of the transformed k-space data;
transform the k-space difference into a difference image;
transform the difference image into a modified difference image by using an inverse of the motion transform between the selected motion bin and the current motion bin; and
update the enhanced image by adding the modified difference image to the enhanced image.
2. The medical imaging system of claim 1, wherein each discrete data portion of the chosen group belongs to one of the predetermined motion bins, wherein when generating the enhanced image, the machine executable instructions further cause the processor to:
calculate the transformed k-space data by transforming of each of the discrete data portions of the chosen group using its corresponding motion transform;

generate combined k-space data by combining k-space data of the selected motion bin with the transformed k-space data of each of the discrete data portions; and
reconstruct the enhanced image from the combined k-space data.

3. The medical imaging system of claim 1, wherein the magnetic resonance data is parallel imaging magnetic resonance data, wherein the difference image incorporates k-space differences from multiple magnetic resonance coil elements, wherein the memory contains coil sensitivity data, wherein execution of the machine executable instructions further causes the processor to correct the reference image for each of the predetermined motion bins by correcting the coil sensitivity data using the motion transform, and wherein the reference image for each of the predetermined motion bins is calculated using the coil sensitivity data.

4. The medical imaging system of claim 1, wherein execution of the machine executable instructions further causes the processor to: bin the discrete data portions into predetermined time bins; and iteratively generate the enhanced image for each of the predetermined time bins by setting the chosen time bin to each of the predetermined time bins.

5. The medical imaging system of claim 4, wherein:
the reference image for initializing the enhanced image for each of the predetermined time bins is identical; and
execution of the machine executable instructions causes the processor to transform the reference image for each of the predetermined time bins to a common motion state using each of the plurality of corresponding motion transforms.

6. The medical imaging system of claim 1, wherein execution of the machine executable instructions further causes the processor to process the modified difference image with a regularization algorithm before adding the modified difference image to the enhanced image.

7. The medical imaging system of claim 1, wherein execution of the machine executable instructions further causes the processor to calculate an elastic registration for the reference image of each of the predetermined motion bins, and wherein the motion transform is interpolated for each current data portion using the elastic registration.

8. The medical imaging system of claim 1, wherein: the sampling pattern is one selected from a group consisting of:
the sampling pattern in k-space is a spiral trajectory;
the sampling pattern in k-space is a linear trajectory;
the sampling pattern is rotated in k-space between sequentially acquired discrete data portions;
the sampling pattern is a Carteisan sampling pattern;
the sampling pattern oversamples a central region of k-space;
the sampling patter is adapted to a motion pattern;
the sampling pattern is randomly or pseudrandomly selected.

9. The medical imaging system of claim 1, wherein the medical imaging system further comprises a magnetic resonance imaging system, wherein the medical imaging system further comprises a subject motion detection system configured for measuring the motion signal value, wherein the memory further contains pulse sequence commands, wherein the pulse sequence commands are configured for acquiring the magnetic resonance data according to a continuous sampling magnetic resonance protocol, wherein execution of the machine executable instructions further causes the processor to:

control the magnetic resonance imaging system with the pulse sequence commands to acquire the magnetic resonance data; and
control the magnetic resonance imaging system to acquire the motion signal during or sequential to acquisition of the magnetic resonance data.

10. The medical imaging system of claim 9, wherein: the subject motion detection system comprises the magnetic resonance imaging system; the pulse sequence commands are adapted for acquiring magnetic resonance navigator data during or sequential to the acquisition of the magnetic resonance data; and execution of the machine executable instructions further cause the processor to calculate the motion signal at least partially using the magnetic resonance navigator data.

11. The medical imaging system of claim 9, wherein the continuous sampling magnetic resonance protocol is a dynamic contrast enhanced magnetic resonance imaging protocol.

12. The medical imaging system of claim 1, wherein the motion transform is a displacement vector field.

13. A method of image processing, wherein the method comprises:
receiving magnetic resonance data, wherein the magnetic resonance data comprises discrete data portions, wherein each data portion comprises an acquisition time and comprises a motion signal value, wherein the discrete data portions have a sampling pattern in k-space, wherein the sampling pattern is rotated in k-space between sequentially acquired discrete data portions;
binning the discrete data portions into predetermined motion bins using the motion signal value of each of the discrete data portions, forming binned discrete data portions;
reconstructing a reference image for each of the predetermined motion bins using the binned discrete data portions;
constructing a motion transform between a selected motion bin and each of the predetermined motion bins using the reference image for each of the predetermined motion bins, wherein the selected motion bin is selected from the predetermined motion bins, forming a plurality of corresponding motion transforms;
binning a chosen group of the discrete data portions into a chosen time bin using the acquisition time of each of the discrete data portions;
generating an enhanced image for the chosen time bin using the chosen group of the discrete data portions and the motion transform of each of the discrete data portions of the chosen group to correct the discrete data portions, wherein the enhanced image is initially the reference image of the selected motion bin, and the method further comprising iteratively generating the enhanced image for each of the discrete data portions of the chosen group by:
choosing a current data portion from the discrete data portions of the chosen group, wherein the current data portion is binned into a current motion bin, wherein the current motion bin is one of the predetermined motion bins;
calculating a transformed image by transforming the enhanced image using the motion transform between the selected motion bin and the current motion bin;
transforming the transformed image into transformed k-space data;

calculating a k-space difference between k-space data of the current data portion and corresponding k-space data points of the transformed k-space data;
 transforming the k-space difference into a difference image;
 transforming the difference image into a modified difference image by using an inverse of the motion transform between the selected motion bin and the current motion bin; and
 updating the enhanced image by adding the modified difference image to the enhanced image.

14. A tangible, non-transitory computer readable medium that stores machine executable instructions, which when executed by a processor, causes the processor to:
 receive magnetic resonance data, wherein the magnetic resonance data comprises discrete data portions, wherein each data portion comprises an acquisition time and comprises a motion signal value, wherein: the discrete data portions have a sampling pattern in k-space, wherein the sampling pattern is rotated in k-space between sequentially acquired discrete data portions;
 bin the discrete data portions into predetermined motion bins using the motion signal value of each of the discrete data portions, forming binned discrete data portions;
 reconstruct a reference image for each of the predetermined motion bins using the binned discrete data portions;
 construct a motion transform between a selected motion bin and each of the predetermined motion bins using the reference image for each of the predetermined motion bins, wherein the selected motion bin is selected from the predetermined motion bins, forming a plurality of corresponding motion transforms;
 bin a chosen group of the discrete data portions into a chosen time bin using the acquisition time of each of the discrete data portions; and
 generate an enhanced image for the chosen time bin using the chosen group of the discrete data portions and the motion transform of each of the discrete data portions of the chosen group to correct the discrete data portions wherein the enhanced image is initially the reference image of the selected motion bin, and iterative generation of the enhanced image is performed by execution of the machine executable instructions repeatedly by the processor that cause the processor, for each of the discrete data portions of the chosen group, to:
 choose a current data portion from the discrete data portions of the chosen group, wherein the current data portion is binned into a current-motion bin, wherein the current motion bin is one of the predetermined motion bins;
 calculate a transformed image by transforming the enhanced image using the motion transform between the selected motion bin and the current motion bin;
 transform the transformed image into transformed k-space data;
 calculate a k-space difference between k-space data of the current data portion and corresponding k-space data points of the transformed k-space data;
 transform the k-space difference into a difference image;
 transform the difference image into a modified difference image by using an inverse of the motion transform between the selected motion bin and the current motion bin; and
 update the enhanced image by adding the modified difference image to the enhanced image.

15. The tangible, non-transitory computer readable medium of claim 14, wherein each discrete data portion of the chosen group belongs to one of the predetermined motion bins, wherein when generating the enhanced image, the machine executable instructions further cause the processor to:
 calculate the transformed k-space data by transforming of each of the discrete data portions of the chosen group using its corresponding motion transform;
 generate combined k-space data by combining k-space data of the selected motion bin with the transformed k-space data of each of the discrete data portions; and
 reconstruct the enhanced image from the combined k-space.

16. The tangible, non-transitory computer readable medium of claim 14, wherein the magnetic resonance data is parallel imaging magnetic resonance data, wherein the difference image incorporates k-space differences from multiple magnetic resonance coil elements, wherein the memory contains coil sensitivity data, wherein execution of the machine executable instructions further causes the processor to correct the reference image for each of the predetermined motion bins by correcting the coil sensitivity data using the motion transform, and wherein the reference image for each of the predetermined motion bins is calculated using the coil sensitivity data.

17. The tangible, non-transitory computer readable medium of claim 14, wherein execution of the machine executable instructions further causes the processor to: bin the discrete data portions into predetermined time bins; and iteratively generate the enhanced image for each of the predetermined time bins by setting the chosen time bin to each of the predetermined time bins.

18. The tangible, non-transitory computer readable medium of claim 14, wherein execution of the machine executable instructions further causes the processor to process the modified difference image with a regularization algorithm before adding the modified difference image to the enhanced image.

* * * * *